United States Patent
Harhay

[19]

[11] Patent Number: 6,040,906
[45] Date of Patent: Mar. 21, 2000

[54] RESONANCE RAMAN SPECTROSCOPY FOR IDENTIFYING AND QUANTITATING BIOMATTER, ORGANIC, AND INORGANIC ANALYTES

[76] Inventor: Gregory P. Harhay, 26 John St., Chicopee, Mass. 01013

[21] Appl. No.: 08/678,649

[22] Filed: Jul. 11, 1996

[51] Int. Cl.[7] .................................................. G01J 3/44
[52] U.S. Cl. ........................ 356/301; 356/302; 356/303; 356/319; 356/326; 356/327
[58] Field of Search .................................. 356/301, 300, 356/302, 303, 311, 319, 322, 327, 326

[56] References Cited

U.S. PATENT DOCUMENTS

| | | | |
|---|---|---|---|
| 4,847,198 | 7/1989 | Nelson et al. | 356/301 X |
| 4,884,886 | 12/1989 | Salzman et al. | 356/367 |

OTHER PUBLICATIONS

Asher, S. A., C. R. Johnson and J. Murtaugh (1983). "Development of a New UV Resonance Raman Spectrometer for the 217–400–NM Spectral Region." *Rev. Sci. Instrum.* 54(12): 1657–62. Summarizes State of RRS as of 1983.

Benevides, J. M. and G. Thomas Jr., J. (1985). "Dependence of Purine 8C–H Exchange on Nucleic Acid Conformation and Base–Paring Geometry: A Dynamic Probe of DNA and RNA Secondary Structures*." *Biopolymers* 24: 667–682. Relates to Hyrdogen Exchange.

Bird, G. R. and W. A. Shurcliff (1959). "Pile–of–Plates Polarizers for the Infrared: Improvement in Analysis and Design." *Journal of Optical Society of America* 49(3): 235–37. Discusses Plate Polarizers.

Dudik, J. M., C. R. Johnson and S. A. Asher (1985). "Wavelength Dependence of the Preresonance Raman Cross Sections of Acetonitrile, Sulfate Ion, Perchlorate Ion and Nitrate Ion." *J. Chem. Phys.* 82(4): 1732–40. Dicusses Raman Cross Sections.

Englander, S. W. and N. R. Kallenbach (1984). "Hydrogen Exchange and Structural Dynamics of Proteins and Nucleic Acids." *Quarterly Review of Biophysics* 16(4): 521–655. Discusses Hydrogen Exchange.

Englander, S. W. and L. Mayne (1992). "Protein Folding Studied Using Hydrogen–Exchange Labeling and Two–Dimentional NMR." *Annual Reviews in Biophysics and Biomolecular Structure* 21: 243–65. Discusses Hydrogen Exchange with Proteins.

Harhay, G. P. (1992). Ultraviolet Resonance Raman Spectroscopy Of The Tertiary Peptide Bond. *Department of Chemistry*. Eugene, Or, University of Oregon: 229. Both invention and the reference discuss RRS.

Hudson, B. and L. Mayne (1986). Ultraviolet Resonance Raman Spectroscopy of Biopolymers. *Methods Enzymol.* 130: 331–50. Change in Raman Spectrum.

(List continued on next page.)

*Primary Examiner*—Frank G. Font
*Assistant Examiner*—Reginald A. Ratliff
*Attorney, Agent, or Firm*—Breffni X. Baggot Intellectual Property Law

[57] ABSTRACT

The invention uses a resonance Raman spectrometer 1 for achieving the identification and quantitation of analytes including biomolecules, organic and inorganic molecules. According to the present invention, a) a sample 2 is deuterated 3 with D20 for facilitating identification and quantitation of analytes 4 of said sample, b) a monochromatic light 6 illuminates sample 2 of analytes 4 for producing Raman sample light 12 and rejecting Rayleigh light 14, c) the Raman sample light 12 is passed through a depolarizer 19 for producing randomized polarization components 20, d) a Raman sample spectrum 22 is generated, calibrated with respect to an absolute differential Raman cross-section standard in response to said randomized polarization components 22, e) the Raman sample spectrum 22 is provided to a spectral analyzer 24 for identification 26 and/or quantitation 28 of the analytes 4.

30 Claims, 16 Drawing Sheets

OTHER PUBLICATIONS

Hudson, B. and L. C. Mayne (1987). Peptides and Protein Sides Chains. *Biological Applications of Raman Spectroscopy: Resonance Raman Spectra of Polyenes and Aromatics.* T. G. Spiro. New York, Wiley. 2: 181–209.

Klawun, C. and C. L. Wilkins (1995). "Neural–Network Assisted Rapid Screening Of Large Infrared Spectral Databases." *Analytical Chemistry* 67(2): 374–378. Neural Nets as They Might Relate to Invention's Use of Spectral Libraries.

Korenowski, G. M., L. D. Ziegler and A. C. Albrecht (1978). "Calculations of Resonance Raman Cross Section in Forbidden Electronic Transitions: Scattering of the 992 CM–1 Mode in the 1B2U Band of Benzene." *J. Chem. Phys.* 68(3): 1248–52. Relates to Raman Cross Sections.

Kubasek, W. L., B. Hudson and W. L. Peticolas (1985). "Ultraviolet Resonance Raman Excitation Profiles of Nucleic Acid Bases with Excitation From 200 to 300 Nanometers." *Proc. Natl. Acad. Sci. U.S.A.* 82(8): 2369–73. pH Dependence of Raman Spectra.

Li, B. and A. B. Myers (1990). "Absolute Raman Cross Sections for Cyclohexane, Acetonitrile, and Water in the Far–Ultraviolet Region." *J. Phys. Chem.* 94(10): 4051–4. Discusses Raman Cross Section Standards.

Mayne, L. C., L. D. Ziegler and B. Hudson (1985). "Ultraviolet Resonance Raman Studies of N–Methylacetamide." *J. Phys. Chem.* 89(15): 3395–8. Change in Solvent on RRS.

Myers, A. B. (1991). "Resonance Raman Depolarization Ratios as a Probe of Ultrafast Excited–State Torsional Dynamics: A Critical Evaluation." *J. Phys. Chem.* 95(4): 1536–8. Relates to Raman Cross Sections and Their Depolarization Ratios.

Myers, A. B. and R. A. Mathies (1987). Resonance Raman Intensities: A Probe of Excited–State Structure and Dynamics. *Biological Applications of Resonance Raman Spectroscopy.* T.G. Spiro. New York, Wiley. 2: 1–58. Spectrometer Independent Spectroscopy.

Nelson, W. H., R. A. Dalterio and S. Peacedale (1989). Detection and Identification of Bacteria by Means of Ultra–Violet Excited Resonance Raman Spectra. *PTO.* USA, The Board of Governors for Higher Education, State of Rhode Island and Providence Plantations. RRS Done on Bacteria.

Nelson, W. H., R. Manoharan and J. F. Sperry (1991). "UV Resonance Raman Studies of Bacteria." *Appl. Spectrosc. Rev.* 27(1): 67–124. RRS Done on Bacteria.

Salzman, G. C., C. T. Gregg, W. K. Grace and R. D. Hiebert (1989). Biological Particle Identification. *PTO.* USA, The United States of America as Represented by the Department of Energy, Relates to Bacterial Identification.

Schomacker, K. T., J. K. Delaney and P. M. Champion (1986). "Measurements of the Absolute Raman Cross Sections of Benzene." *Journal of Chemical Physics* 85(8): 4240–47. Discusses Local Field Correction.

Schulze, H. G., M. W. Blades, A. V. Bree, B. B. Gorzalka, L. S. Greek and R. F. B. Turner (1994). "Characteristics of Backpropagation Neural Networks Employed in the Identification of Neurotransmitter Raman–Spectra." *Applied Spectroscopy* 48(1): 50–57. Relates to Raman Spectra and Their Uses with Neural Nets.

Sension, R. J. and H. L. Strauss (1986). "Comparison of Experiment and Theory for the Resonance Raman Excitation Profile of Diatomic Iodine in N–Hexine." *J. Chem. Phys.* 85(7): 3791–806. Depolarization Ratio Changes with Excitation Frequency.

Siebrand, W. and M. Z. Zgierski (1982). "Effect of Solvent–Induced Line Broadening on Resonance Raman Excitation Profiles and Depolarization Ratios." *J. Phys. Chem.* 86(24): 4718–25. Why Depolarization Ratio Changes with Excitation Frequency.

Siragusa, G. R., C. N. Cutter, W. J. Dorsa, and M. Koohmaraie (1995). "Use of a Rapid Microbial ATP Bioluminescence Assay to Detect Contamination on Beef and Pork Carcasses." *J. Food Prot.* 58: 770–775. Discusses Sample Prep of a Beef Menstrua Solution.

Smith, S. O., M. S. Braiman, A. B. Myers, J. A. Pardoen, J. M. L. Courtin, C. Winkel, J. Lugtenburg and R. A. Mathies (1987). "Vibrational Analysis of the All–Trans–Retinal Chromophore in Light–Adapted Bacteriorhodopsin." *J. Am. Chem. Soc.* 109(10): 3108–25. Relates to RRS Done on Bacteriarhodopsin.

Tanabe, K., T. Tamura and H. Uesaka (1992). "Neural Network System for the Identification of Infrared Spectra." *Applied Spectroscopy* 46(5): 807–10. Relates to Patent Appliction's Discussion of Neural Nets for Bacterial Identification.

Womack, J. D., C. K. Mann and T. G. Vickers (1989). "Correction for Absorption in Raman Measurements Using the Backscattering Geometry." *Applied Spectroscopy* 43(3): 527–31. Relates to Self–Absorption Correction.

Ziegler, L. D., B. Hudson, D. P. Strommen and W. L. Peticolas (1984). "Resonance Raman Spectra of Mononucleotides Obtained with 266 and 213 NM Ultraviolet Radiation." *Biopolymers* 23(10): 2067–81. Discusses excitation frequency effects on RRS of DNA and RNA and mononucleotides.

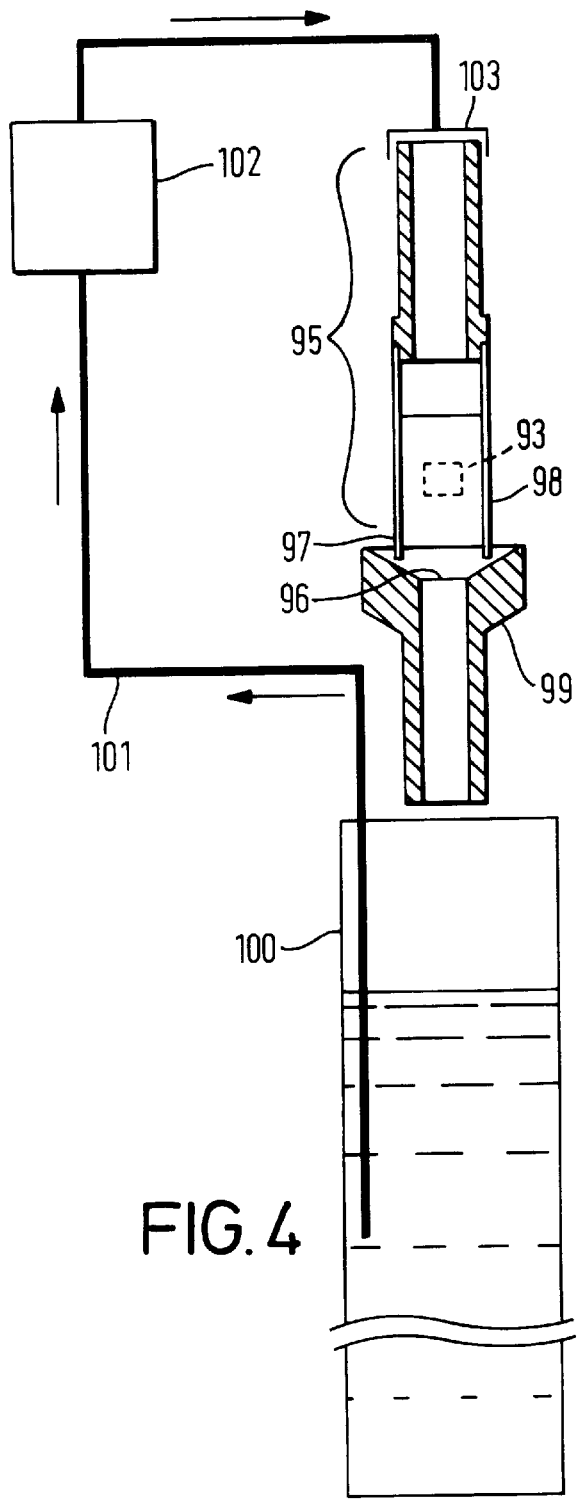
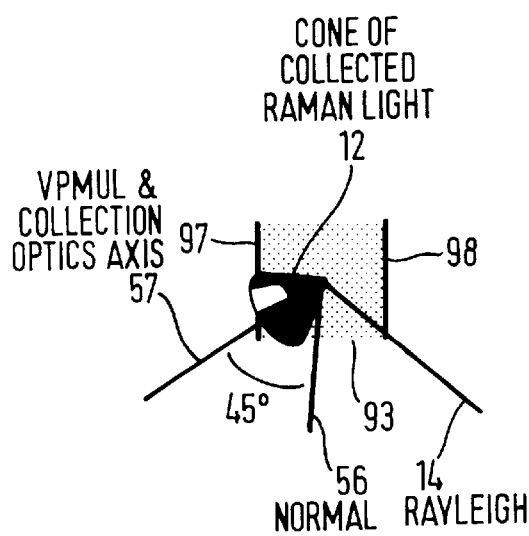
FIG. 4A
FIG. 4

A - With Depolarizer

B - Without Depolarizer

RESONANCE RAMAN SPECTROSCOPY FOR IDENTIFYING AND QUANTITATING BIOMATTER, ORGANIC, AND INORGANIC ANALYTES

FIELD OF INVENTION

This invention relates to resonance Raman spectroscopy.

BACKGROUND OF THE INVENTION

Recent outbreaks of pathogenic *E. Coli* 0157:H7 poisoning in humans from the ingestion of tainted meats has created great interest in establishing rational and scientifically tested criteria for approving meat and poultry for human consumption. At the present time, most methods in use providing the necessary selectivity and sensitivity necessary to detect the presence of pathogenic bacteria in or on beef or poultry require 24–48 hr's. Test that take this long are based upon classical bacteriological techniques that require samples taken from beef or poultry be grown up in cultures for bacteriological identification and quantification. A new instrument that utilizes the polymerase chain reaction (PCR) for bacterial identification is being marketed by Dupont under the trade name Ribo-Printer. This instrument/method takes at least 8 hours to obtain a result.

In "Biological Particle Identification Apparatus" invented by Gary C. Salzman, Charles T. Gregg, W. Kevin Grace, Richard D. Hiebert, U.S. Pat. No. 4,884,886 awarded in Dec. 5, 1989, these inventors show that multiparameter light scattering measurements can be used to identify biological particles such as bacteria and viruses in pure homogeneous solutions. This requires that each of the particles to be identified be purified prior to analysis. This technique cannot work with heterogeneous samples and is therefore unsuitable for quickly identify and quantify bacterial pathogens in beef menstrua in the slaughterhouse.

In "Detection And Identification of Bacteria By Means Of Ultra-Violet Excited Resonance Raman Spectra", invented by Wilfred H. Nelson, Richard A. Dalterio, and Sperry Peacedale, U.S. Pat. No. 4,847,198, awarded on Jul. 11, 1989 these inventors have shown that resonance Raman spectra of pure cultures of bacteria exhibit taxonomic identifiers. By collecting resonance Raman spectra as a function of laser excitation frequency, these inventors claim a method of taxonomic identification using the excitation behavior of the Raman spectra of the species in question. The excitation behavior is the behavior of the resonance Raman spectra of the same sample as the excitation frequency is varied. These inventors used a quartz capillary as a sample holder through which the analyte solution was flowed, and upon which the laser excitation beam was impinged. The Raman light can be collected in a geometry from 0 to 90 degrees from the collection optical axis.

What this solution gives with one hand it takes away with the other. The design of the Raman system in this patent is subject to spectral artifacts due to laser induced photodecomposition of the quartz capillary, as well as denaturation and photodecomposition of the biomolecules at the quartz-liquid interface. This may cause changes in the biomolecules' resonance Raman spectra. Furthermore, this invention doesn't include a polarization scrambler at the entrance to the monochrometer. The lack of a polarization scrambler can lead to anomalous spectra, because the gratings and mirrors in a monochrometer preferentially pass light of a given polarization with higher relative efficiency than another polarization. A grating monochrometer therefore, exhibits polarization bias that must be removed if the results from one monochrometer configuration can be compared to another. Furthermore, when comparing spectra or the absolute differential Raman cross-sections of Raman bands obtained at different excitation frequencies, a depolarizer must be employed so that the observed changes in these observables remain unaffected by the polarization bias of the monochrometer. Thus, the excitation behavior of resonance Raman spectra and the absolute differential Raman cross-sections of the Raman bands in the spectra are reliable only if a depolarizer is used in conjunction with a grating monochrometer.

DEFINITIONS ns: nanosecond, 10-9 second
nm: nanometer, 10-9 meter
cm-1: wavenumber, 1 cm
O.D.: optical density
BT: *Brochothrix thermosphacta* American Type Culture Catalogue number 11509
PF: *Pseudomonas fluorescens* American Type Culture Cataloge number 13525
beef menstrua: the constituents found on the surface of a beef carcass
polarizance: equal to the degree-of-polarization that the polarizer produces in an incident monochromatic beam that is unpolarized

DISCLOSURE OF THE INVENTION

Objects of the present invention include the taxonomic identification and quantitation of bacteria and/or biomolecules and quantitation and identification of inorganic and/or organic compounds having exchangeable protons.

The present invention is predicated on the observation that for any pathogen detection system to be commercially viable, it must be a) quick on the order of seconds to minutes, b) sensitive, c) be able to identify and quantify bacteria in heterogeneous samples consisting of bacteria, blood, fat, muscle, excrement, and other components in beef menstrua, d) able to distinguish between pathogenic and non-pathogenic organisms, e) inexpensive on a per test basis, as well as well as f) minimizing the requirements for highly trained personnel and expensive reagents. It is imperative that the number of carcasses tested, as well as the total number of bacteriological tests, be dramatically increased to improve the safety of the United States' meat and poultry supply. The test must should be conducted in the slaughterhouse on the processing line.

The present invention is predicated on the observation that resonance Raman spectra of two different bacteria may be similar when the bacteria sit in an aqueous buffer but differ when the bacteria are deuterated.

According to the present invention, a) a sample of analytes is deuterated with D20 for facilitating identification and quantitation of analytes of said sample, b) a monochromatic light illuminates a sample of analytes for producing Raman sample light and rejecting Rayleigh light, c) the Raman sample light is passed through a depolarizer for producing randomized polarization components, d) a Raman sample spectrum is generated, calibrated with respect to an absolute differential Raman cross-section standard in response to said randomized polarization components, e) the Raman sample spectrum is provided to a spectral analyzer for identification and/or quantitation of the analytes.

One advantage of the present invention is that quantitation and identification of biomolecules and bacteria may be accomplished on the order of seconds to minutes rather than hours or days.

Another advantage of this invention is that the sample handling apparatus in this invention minimizes spectral artifacts due to photodecomposition and biomolecular denaturation of the analyte.

A feature of the present invention is that the invention achieves its objects regardless of the parameters of the equipment used to obtain the Raman spectrum.

Still further objects and advantages will become apparent from a consideration of the ensuing description and accompanying drawings.

BRIEF DESCRIPTION OF THE DRAWINGS

FIG. 4 is a schematic of a reservoir for holding the analytes.

FIG. 4A is close up view of FIG. 4A in the region where monochromatic light hits an analyte-containing sample.

BEST MODE FOR CARRYING OUT THE INVENTION

ACQUISITION OF THE EXPERIMENTAL RAMAN SPECTRUM USING THE RAMAN SPECTROMETER

Figures 1, 1A:
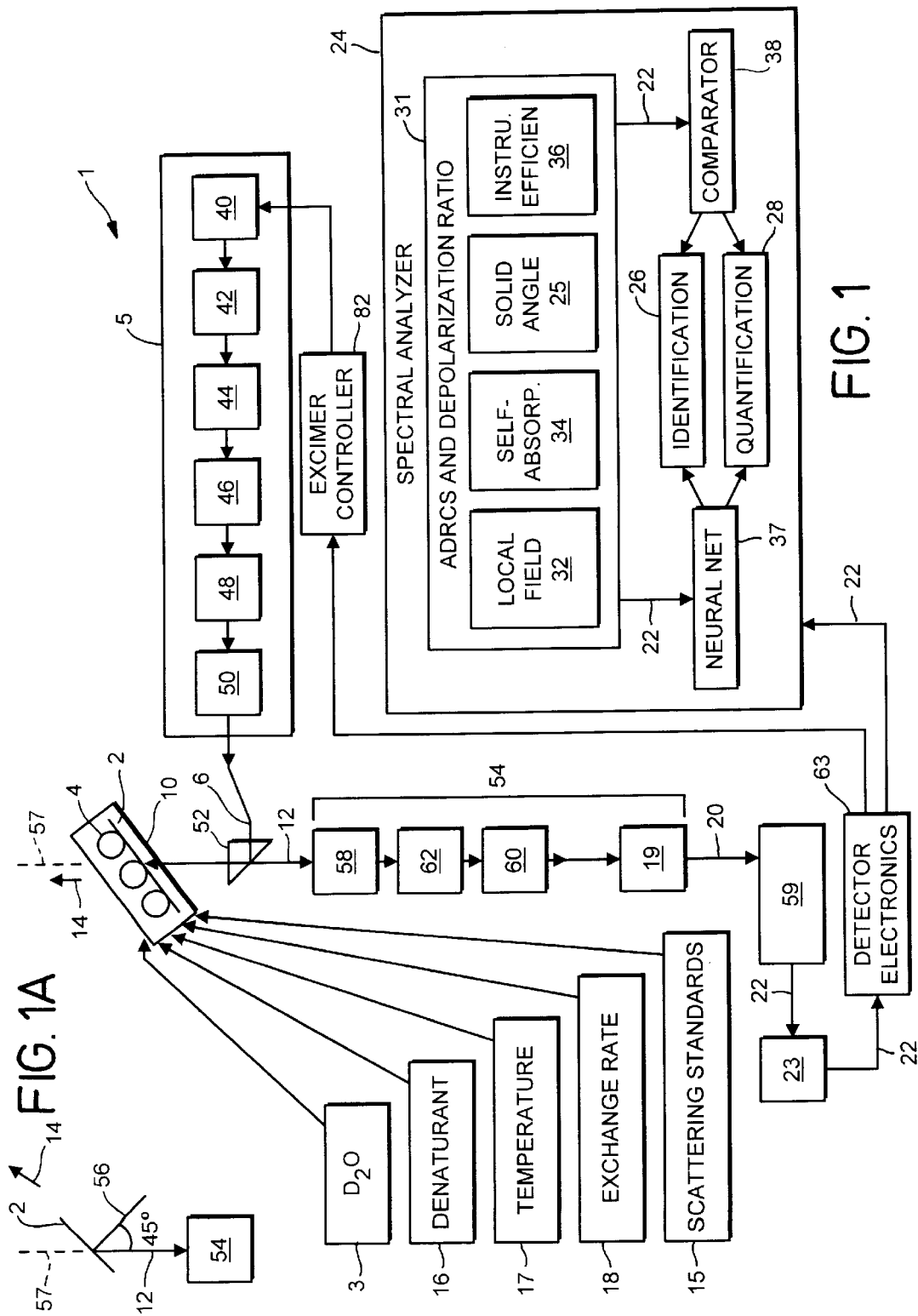
FIG. 1 is plan view of the resonance Raman spectrometer according to the present invention for quantifying and identifying analytes.
FIG. 1A is a closeup view of the sample.

FIG. 1 shows a Raman spectrometer 1 for using resonance Raman spectroscopy for achieving the identification and quantitation of biomolecules, organic and inorganic molecules. First, a sample 2 is deuterated with deuterium (D20) 3. The sample 2 contains one or more analytes 4, each analyte 4 having exchangeable protons such that said deuteration will cause the protons of said analyte to be exchanged with deuterons for facilitating identification of said sample. Hereafter it is understood that the term analytes is interchangeable with bacteria, viruses, prions, biomolecules, biomolecular assemblies, inorganic and organic compounds and vice versa.

In FIG. 1, next, an excitation frequency of a laser light source 5 provides monochromatic light 6 onto sample 2 contained in a reservoir 10 for providing sample Raman light 12 while rejecting Rayleigh light 14.

For altering the extent of deuteration, increasing the speed of identification/quantitiation of the analytes 3, the reservoir 10 may be responsive to a number of controls. The reservoir 10 includes, one or more analytes 3 including beef menstrua, prions, bacteria, organic and inorganic molecules, proteins, nucleic acids and other biomolecules. Second, the reservoir 10 also contains one or more standards 15 for normalizing/calibrating analysis of the Raman spectra 12 of analytes 4 in sample 2. This is similar to standards used in IR and NMR analysis of organic compounds. The reservoir also may contain one or more denaturants 16 for denaturing the analytes 3. Third, the reservoir 10 may be responsive to temperature control 17. Fourth, an exchange rate control 18 may control the rate of deuterium (D20) exchange with analyte 8 protons. This is done in a process analogous to varying pH. It is an analogous process since pH in a D20/water solution has a different connotation from pH in solutions where D20 is not used. The sample Raman light 12 is passed through a depolarizer 19 for producing randomized polarization components 20. A Raman sample spectrum 22 is generated—calibrated with respect to an absolute differential Raman cross-section standard 15 in response to said randomized polarization components 20. The Raman sample spectrum 22 is provided through a detector 23 to a spectral analyzer 24 for identification 26 and/or quantitation 28 of the analytes 3. Spectral analyzer 24 includes a block 31 for calculating an absolute differential Raman cross-section (ADRCS) and for calculating a depolarization ratio. Block 31 has features for improving the performance of spectral analysis including a local field correction 32, a self-absorption correction 34, a solid angle correction 35 and an instrument efficiency correction 36. The spectral analyzer 24 contains a computer(not shown) and the usual elements for analyzing resonance Raman spectra. Block 31 provides the ADRCS and Raman spectra 22 to a neural network 38 and spectral comparator 38. Both are for identifying and quantitating the analytes 3 in response to the ADRCS or Raman sample spectra 22. The comparator compares the Raman sample spectra 22 to a known Raman sample spectra and thereby determines the identity of the analytes. For example, the Raman sample spectra 22 may be compared to the spectra or sum of spectra for BT and PF. If there is a match, then BT and PF are determined to be the analytes 3. The comparator 38 includes a spectral library with the known resonance Raman spectra of millions of known bacteria, viruses, preons, biomolecules, inorganic and organic compounds and other proton-bearing chemical species. The neural network 37 achieves the same result—identification and quantitation—using well known training algorithms typical of neural networks. The Raman spectrometer 1 in FIG. 1 is more fully described. An excimer laser 40 generates 1–2 nanosecond light pulses of 308 nm light at a rate between 50 to 400 Hertz. These pulses are directed into a dye laser 42. For the experiments presented here, the excimer laser 40 pumps dye laser 42 to produce 444 nm laser pulses. The light pulses generated by the excimer in the dye laser 42 are passed through a beta barium borate second harmonic generation (BBO SHG) crystal 44, decreasing the wavelength of the laser light by ½. An arrangement of Pellam-Brocca prisms 46 separates the 222 nm light from the 444 nm light. The combination of the excimer laser 40, the tuneable dye laser 42, the second harmonic generation crystal 44, and the Pellam-Brocca prisms 46, is referred to as a laser light source 4. The 222 nm light passes through a Glan-Taylor prism 48 to produce a vertically polarized monochromatic ultraviolet light (VPMUL) beam, the monochromatic light 6. The monochromatic light 6 is then focused by an adjustable laser focusing lens 50 through a 5 mm 90 degree S1-UV prism 52 at a sample 2. The combination of the Glan-Taylor prism 48, the laser focusing lens 50, and the steering prism 52, is referred to as a laser steering optic. The position of the focus of the monochromatic coherent light 6 and sample 2 are adjusted to be coincident with the focus of collection optics 54.

The sample 2 is a flat approximately 2 mm thick planar stream of liquid that is not contained by windows of the reservoir 10. A normal 56 to the stream is oriented 45 degrees with respect to the collection optic axis 57. The angle present in FIG. 1 is shown in separate FIG. 1A. When the monochromatic light 6 impinges upon the windowless sample stream 2, elastically scattered laser light Rayleigh 14 is directed away from an f/1 S1-UV biconvex 2" diameter collection lens 58, while the sample Raman light 12 (that is scattered omnidirectionally by the sample 2 is collected by the f/1 S1-UV biconvex 2" diameter collection lens 58. The sample Raman light 12 is then focused ultimately onto monochrometer 59 at an entrance slit with an f/6.5 S1-UV biconvex 2" diameter lens 60. This lens 60 f-matches the f-number of the detector 23. A depolarizer 19 is placed between the f/6.5 S1-UV biconvex 2" diameter lens 60 and monochrometer 59 to scramble the polarization of the sample Raman light 12. This is necessary to remove any monochrometer59/detector19 bias for a specific polarization of sample Raman light 12. If the depolarizer 19 is not present, excitation dependent Raman spectral intensities of Raman bands in the sample Raman light 12 may show anomalous behavior. Furthermore, this depolarizer 19 is a necessary prerequisite for the direct comparison of the data between two or more non-identical monochrometers 59. The combination of the collection lens 58, the focusing lens 60, and the depolarizer 19 is referred to as the Raman collection optic 54.

Depolarization ratios can be measured by inserting a stacked plate polarizer 62 between f/1 S1-UV biconvex 2" diameter collection lens 58 and f/6.5 S1-UV biconvex 2"

diameter lens 60, concentric with the optic axis. The stacked plate polarizer 62 consists of 18 4"×2" S1-UV Suprasil plates(not shown but known in the art). The parallel and perpendicularly polarized components 20 of the sample Raman light 12 are measured by placing the polarizer 62 along the optic axis, measuring either parallel or perpendicular component, and rotating the polarizer 62 about its long axis 90 degrees to measure the other polarization component. The sample Raman light 12 passes through the depolarizer 19 and enters the monochrometer 59 where it is ispersed.

The Raman spectrum 22 is provided to spectrum analyzer 24. The spectrum analyzer 24 can take several forms as those skilled in the art of spectral analysis would appreciate.

Control of the detector 23 by detector electronics 63 can take many forms. Two are explained here.

Figure 2:
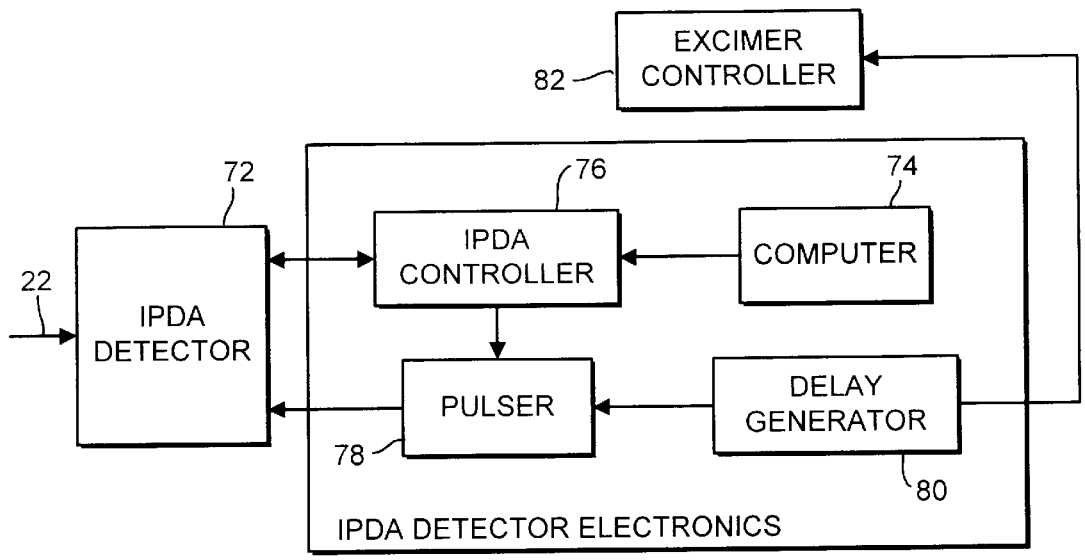
FIG. 2 is bock diagram of one embodiment of a detector electronics shown in FIG. 1

The detector 23 can be an intensified photodiode array (IPDA) detector 72. In FIG. 2, the Raman spectrum 22 is focused on an intensified photodiode array (IPDA) detector 72 and transferred to a dedicated computer 74 via interface controller 76. The Raman spectrum 82 falls on the IPDA detector 72 for a selectable time to produce an adequate signal to noise spectrum, then computer controlled dedicated spectral processing software specific for each detector 72 reads the detectors 72, and saves the Raman spectrum 22 in the computer 74. The display of this information in graphical form (spectrum) whose ordinate is proportional to photon flux with an abscissa in wavenumbers, or in a tabular form, is well within the scope of those skilled in the art. The IPDA detector 72 can be operated in gated mode, its exposure synchronized with the laser pulses. For instance, the human operator initiates the experiment at the computer 74 that transmits a signal through an IEEE-488 interface to the controller 76 that in turn activates a high voltage pulser within the ICCD controller 76 that applies high voltage gating pulses to expose the detector to the dispersed Raman light 22 at a frequency and gating width determined by the delay generator 80. The delay generator 80 also sends a triggering pulse to the excimer laser controller 82, the application of the high voltage to IPDA detector 72 is delayed relative to the excimer laser triggering pulse to maximize the Raman signal accumulated at the detector 72. At the conclusion of a predetermined data acquisition time, IPDA 72 is read and the spectral information transferred to the computer 74 via the IPDA controller 76.

Figure 3:
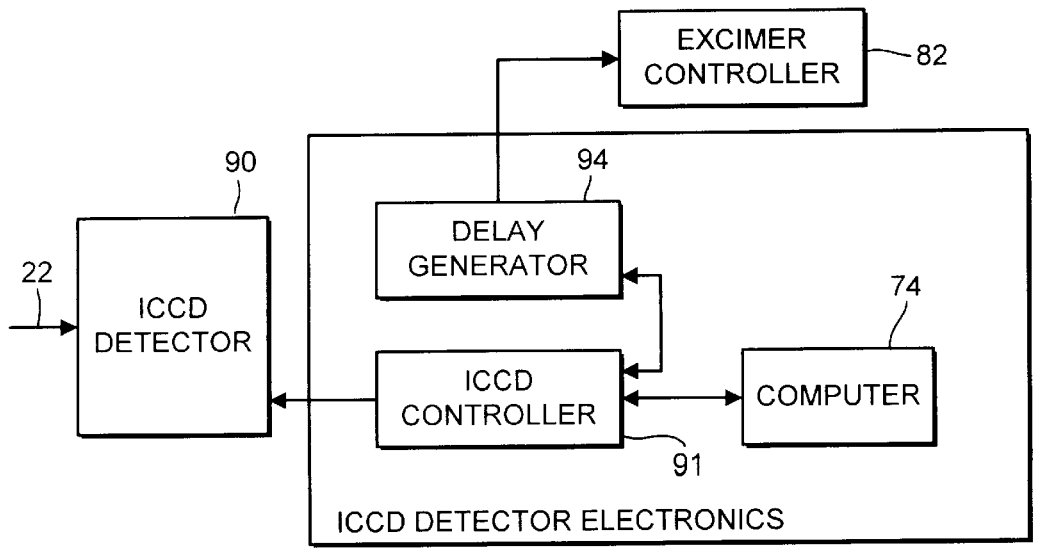
FIG. 3 is a block diagram of another embodiment of the detector in FIG. 1.

FIG. 3 shows a slightly modified apparatus to collect resonance Raman spectra of bacteria. Detector 23 can be an ICCD 90. This FIG. 3 apparatus is modified to use a intensified charge couple device detector (ICCD) 90 to detect the sample Raman light 12. The difference between the apparatus in FIGS. 2 and 3 are detector control—the electronics used to control and acquire data from ICCD 90. The detector 90 was operated ungated. The human operator initiates the experiment at the computer 74 that transmits a signal to the ICCD controller 90 that controls the application of high voltage potential generated in the ICCD 90 to expose the ICCD 90 to the dispersed sample Raman light 12 for the duration of the data acquisition time. Delay generator 94 sends a triggering pulse to the excimer laser controller 76 to fire the laser at a predetermined repetition rate. At the conclusion of a predetermined data acquisition time the high voltage potential is removed from the ICCD 90, the data is read from the ICCD 90, and the spectral information transferred to the computer 4 via the ICCD controller 91.

RESERVOIR

FIG. 4 shows how monochromatic light 6 (FIG. 1) is caused to irradiate sample 2 in a region 93. The reservoir 10 sample handling apparatus in is fully described in FIG. 4. FIG. 4 shows the how the sample 2 in a windowless sample stream 93 is formed by the planar flow device 95. Liquid is circulated through the planar flow device 95 where it exits through a narrow slit 96, on each side of which are two quartz capillary tubes, tube 97 and tube 98. Both of these tubes 97, 98 serve to form a planar sheet of liquid sample 2 between these tubes 97, 98 as the liquid sample 2 flows down towards the funnel 99. The liquid sample 2 flows through the funnel 99 into the test tube 100. The liquid sample 2 is pumped from the test tube 100 through the Teflon tubing 101 with the pump 102 and is directed into the planar flow device 95 through the device cap 103. With this arrangement of FIG. 4, the sample 2 can be recirculated in front of the monochromatic light 6 (FIG. 1) indefinitely. Flowing the sample 2 in front of the monochromatic light 6 reduces the risk of photodecomposition of the sample, as the monochromatic light 6 does not irradiate exactly the same sample molecules with every pulse of monochromatic light 6. The decomposition of the reservoir 10 at the sample container/sample/laser interface is eliminated. If this interface is present, the sample 2 in the region 93 has a propensity to photodecompose at the interface. This eventually produces discolored spots of photodecomposed sample and window material that can give anomalous results, i.e. resonance Raman of photodecomposed sample and or window material. Often the window is made of highly polar substances, such as glass and quartz, these material are known to bind polar biomolecules such as proteins and nucleic acids. This association of the biomolecules with the widow material can denature these molecules, altering their Raman spectra. Elimination of the window material reduces the possibility of spectral artifact due to biomolecular denaturation. The reservoir 10 described here also treats the sample 2 gently, unlike similar designs in the literature that employ dye jets. The sample 2 is flowed through the system slowly, 10–30 ml/minute. This slow flow rate, gentle handling mode is required when working with biological samples so as to reduce the risk of denaturation of the biopolymers present in the sample 2. Another positive attribute of the slow flow rate is the smoothness and flatness of the surface of the windowless stream of sample 2. The smoother and flatter the stream of sample 2, the better the Rayleigh rejection. The 45 degree angle of the normal of the windowless sample stream 2 with respect to the collection optic axis efficiently rejects the Rayleigh scattering 14, removing the need present in the Nelson et al. patent (see Background) for a cuvette filled with a quinoline solution in front of the entrance slit to reject the Rayleigh light. The quinoline solution can distort the observed spectrum by preferentially absorbing light in one or more regions of the observed Raman spectrum. This effect must be taken into account for quantitative measurements of the Raman cross-section to be reliable.

FIG. 4A illustrates the VPMUL monochromatic light 6 incident on the sample in the region 93 at an angle 45 degrees from the axis of the collection optic 57 for producing a cone of sample Raman light 12 and rejecting Rayleigh light 14.

SAMPLE PREPARATION

Preparation of the sample 2 in FIG. 1 is necessary to acquire quantitative resonance Raman spectra and is described below. In addition, calibration of the resonance Raman spectrometer 1 is required. Three calibration standards are used: a Raman cross-section standard, a wavelength standard, and a depolarization ratio standard.

BUFFER CONTAINING ABSOLUTE RAMAN CROSS-SECTION STANDARD

Buffer solutions of 0.15 M Na2SO4, 0.20 M Na2HPO4 and adjusted with HCl to pH 7.25 were prepared. The Na2SO4 is the absolute Raman cross-section standard.

PREPARATION OF BEEF MENSTRUA SOLUTIONS

Beef menstrua samples were sponged off of a 500 cm2 area of a beef carcass, and squeezed into a test tube. The sponged was presoaked with a mixture of TWEEN and NaCl. A mixed culture of bacteria isolated from beef carcasses was added in to the beef menstrua. Beef menstrua samples were sponged off of a 500 $cm^2$ area of a the brisket region of beef carcass with a microbial sampling sterile sponge moistened with 25 ml of 0.085% (wt/vol) NaCl+ 0.05% (vol/vol) Tween 20 adjusted to pH 7.8 in a Whirlpak bag. The solution was expressed from the sponge as it was removed from the bag. The sponge was wiped over the sample area 10 times in both the vertical and horizontal direction, with the collected beef menstrua expressed into a test tube. A mixed culture of bacteria isolated from beef carcasses was added to the beef menstrua.

PREPARATION OF BACTERIAL SOLUTIONS

Pure cultures of Brochothrix thermosphacta ATCC 11509 and *Pseudomonas fluorescens* ATCC 13525 were carefully swabbed off of slants and suspended in a buffer of 0.15 M Na2SO4, 0.20 M Na2HPO4 and adjusted with HCl to pH 7.25. These suspensions are referred to the stock bacterial solutions. The optical densities of these suspensions were measured at 600 nm to determine approximate bacterial concentration in the stock solutions. The stock bacterial cultures and the beef menstrua/bacterial solutions were either mixed with 0.15 M Na2SO4, 0.20 M Na2HPO4 pH 7.25 in water (H20) or 0.15 M Na2SO4, 0.20 M Na2HPO4 pD 7.25 in heavy water (D20). The SO4-2 ion serves as internal Raman cross-sections standard as well as the depolarization ratio standard. Typically, 2 ml of menstrua or bacterial culture stock were mixed with the water or heavy water buffer to bring the total volume up to 12.0 ml.

SPECTRAL CALIBRATION

To acquire quantitative resonance Raman spectra, the Raman spectrometer is be calibrated with spectral standards for wavelength and polarizance. This calibration procedures are described below.

WAVELENGTH CALIBRATION

Wavelength calibration 1 was accomplished in the following manner. The spectra were wavelength calibrated by first acquiring the spectra of neat acetonitrile, using the 918 and 1372 cm-1 bands to convert from diode or pixel number to wavenumber. The spectra of BT and PF presented here were baseline subtracted. All total intensity measurements were normalized to the 981 cm-1 band of the internal standard, SO4-2 ion, setting its peak height to 1.000.

POLARIZANCE CALIBRATION

The depolarization ratio of a Raman band, analyte, standard or other, alluded to in FIG. 1 is defined to be:

$$\rho = \frac{I_{perpendicular}}{I_{parallel}} \quad \text{Equation 1}$$

Figure 5:
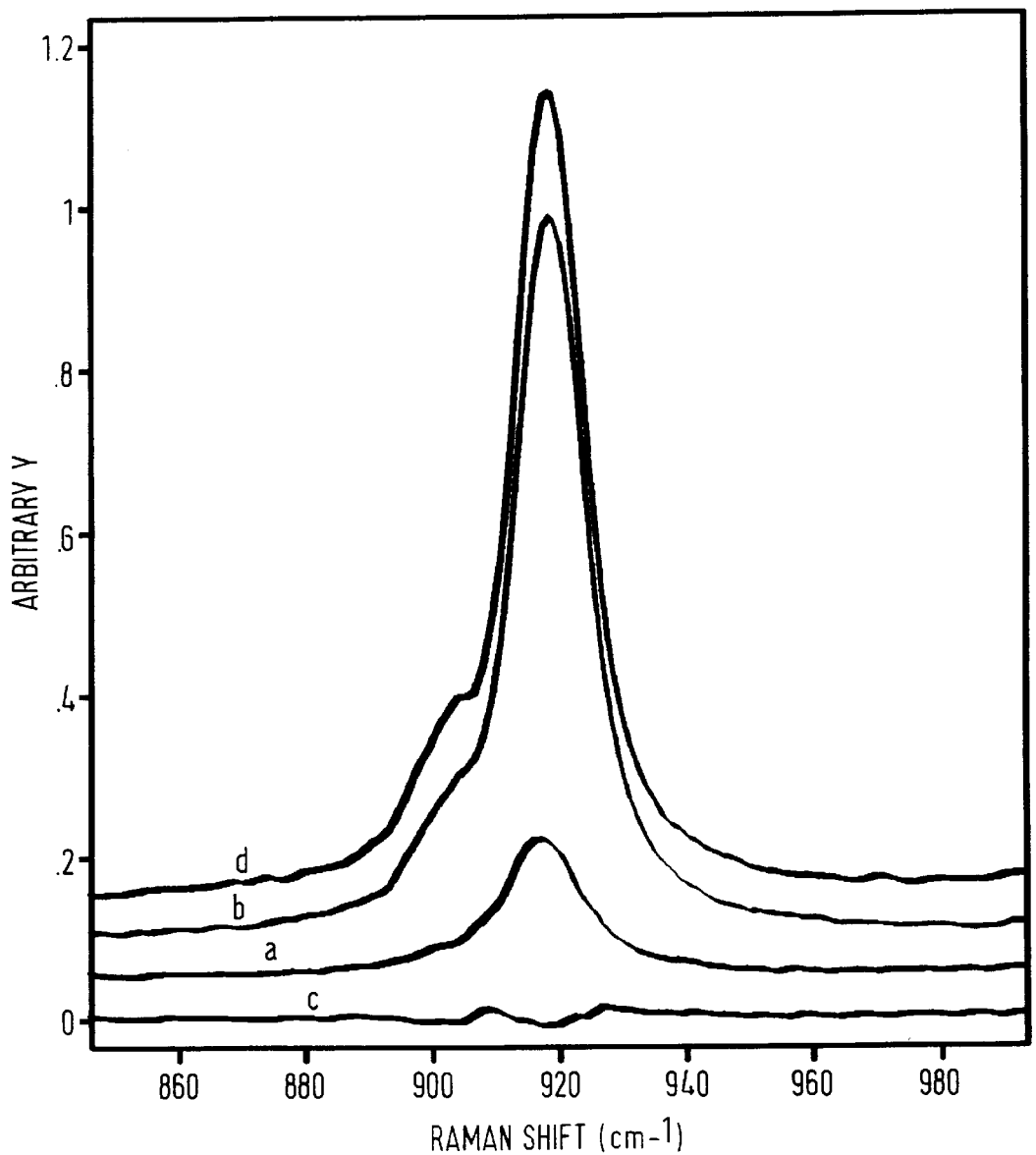
FIG. 5 is a representation of the polarization components of the Raman spectrum of acetonitrile at 222 nm excitation, the ordinate is scale is normalized to the height of the 932 cm-1 band in the measured total intensity spectrum and the abscissa scale is Raman shift, cm-1. The polarization components of acetonitrile shown are (a) the measured perpendicular component spectrum, (b) the measured parallel component spectrum, (c) the calculated corrected perpendicular component spectrum, and (d) the calculated total intensity spectrum of acetonitrile at 222 nm excitation. This representation shows the polarization components used to produce the calculated perpendicular and total intensity spectra.

FIG. 5 shows the (a) measured perpendicular component spectrum, (b) the measured parallel component spectrum, the (c) calculated perpendicular component spectrum, and (d) the calculated total intensity spectrum of acetonitrile at 222 nm excitation. The depolarization ratio measurements have limited precision because a limited solid angle of Raman light 27 is collected, and light leakage of the parallel component of the Raman light 27 through the polarizer 34 when measuring the perpendicular component. This leakage of one polarization component through the polarizer when measuring the other polarization component is related to the polarizance of the polarizer defined equal to the degree-of-polarization that the polarizer produces in an incident monochromatic beam that is unpolarized. This leakage of the wrong polarization component through the polarizer is approximately corrected for in following manner. The depolarization ratio, p, of the 918 cm-1 band of acetonitrile and of the 981 cm-1 band of SO4-2 was measured to be no greater than 0.05 between 220 and 300 nm. These authors state that these depolarization ratios are probably less than 0.05. Since the precision of the depolarization ratio measurements with the stacked plate polarizer is limited, with p =0.05 indistinguishable from $\rho$=0; the value of $\rho$ was set to 0. The residual transmittance of the polarizer was removed from the (a) perpendicular component spectrum by subtracting 0.2×the (b) parallel component spectrum from perpendicular spectrum to bring the intensity of the 918 cm-1 line of acetonitrile in the (c) corrected perpendicular component spectrum to 0. This subtraction process can be verified by adding the (c) corrected perpendicular component to the (a) parallel component to produce a (d) calculated total intensity spectrum. Because of scattering losses in the polarizer, the calculated total intensity spectrum exhibits lower intensity Raman bands than those in the measured total intensity spectrum measured without a depolarizer.

Figure 6:
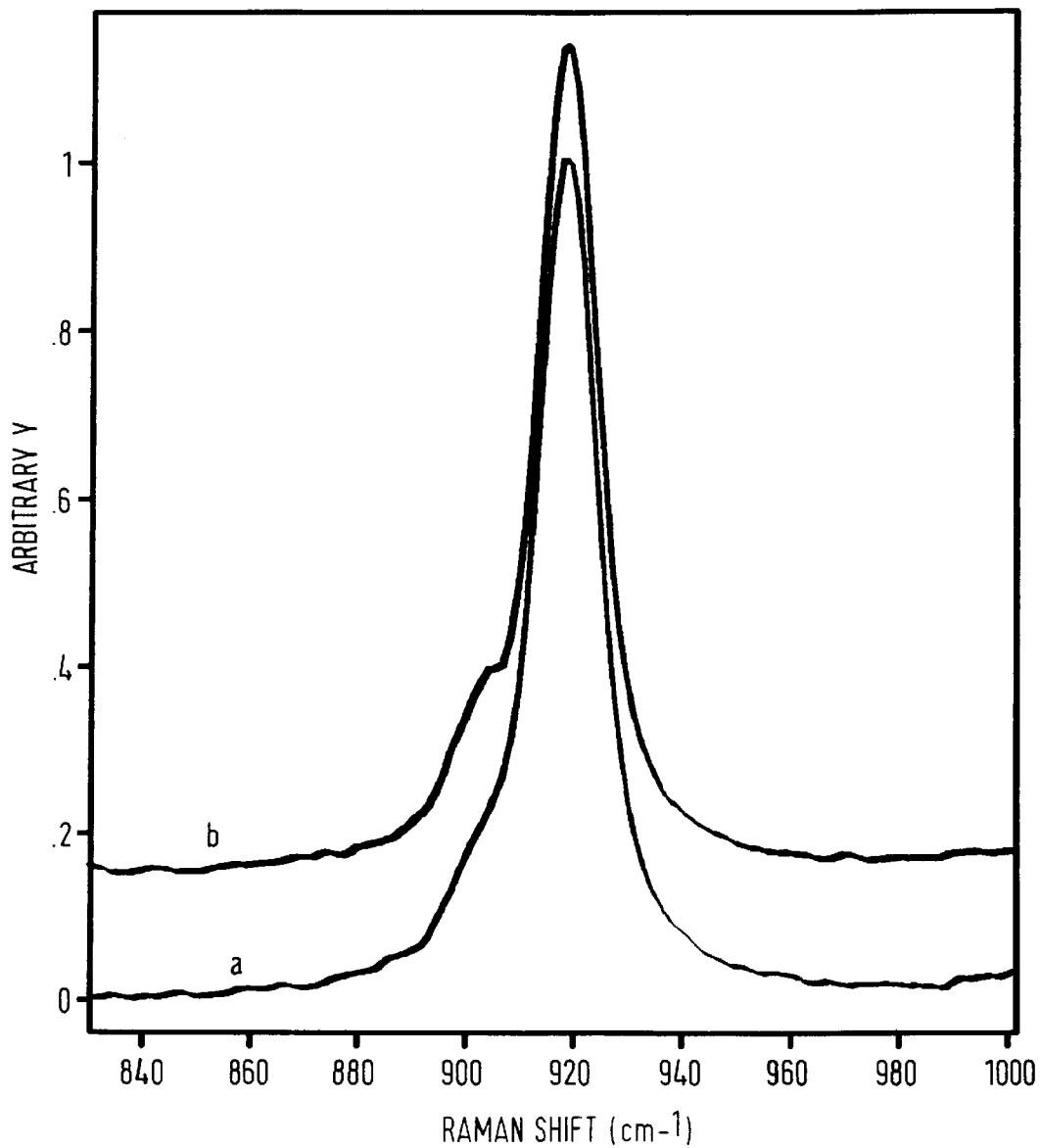
FIG. 6 is a representation of the (a) measured total intensity spectrum and (b) calculated total intensity spectrum of acetonitrile at 222 nm excitation, the ordinate scale for both the measured and calculated total intensity spectrum are normalized to the height of their respective 981 cm-1 band and the abscissa scale is Raman shift, cm-1. This representation shows the near equivalence of the calculated and measured total intensity spectrum, verifying the methods used to calculate the corrected perpendicular component spectrum.

FIG. 6 shows the (a) normalized measured total intensity spectrum, normalized with respect to the 981 cm-1 band height and (b) calculated total intensity spectrum (setting the height of 981 cm-1 band to 1.000). These two spectra nearly overlap. This confirms that the method of calculating the corrected perpendicular component spectrum yields acceptable results. If the results were unacceptable, the spectra wouldn't overlap, when the heights of the 981 bands were made to be equal to 1, the baselines would be off, or the width of the bands would be off.

CALCULATION OF THE ABSOLUTE RAMAN CROSS-SECTION FROM EXPERIMENTAL DATA

Next in the identification 26 and quantification 28 of bacteria and other analytes 3 (FIG. 1) is the calculation of the absolute differential Raman cross-section(ADRCS) and depolarization ratio of Raman bands of the bacteria and other analytes in sample 2. This calculation requires that instrument efficiency 36, solid angle 35, local field 32, and self-absorption 34 corrections need to be considered.

The calculation of the absolute differential Raman cross-section (ADRCS) and the corrections 32, 34, 35, 36 are discussed in this section. The absolute differential Raman cross-sections of the bacteria or any analyte 3 is given by the following equation:

$$\left(\frac{d\sigma}{d\Omega}\right)_{bac} = \left(\frac{d\sigma}{d\Omega}\right)_{std} \frac{I_{bac}}{I_{std}} \frac{E(\tilde{\upsilon}_{laser} - \tilde{\upsilon}_{bac})}{E(\tilde{\upsilon}_{laser} - \tilde{\upsilon}_{std})} \frac{C_{std}}{C_{bac}} \frac{L(bac+std)}{L(std)} \left(\frac{n_{std}}{n_{bac}}\right)^2 (Self-Abs)$$   Equation 2 where:

$$\left(\frac{d\sigma}{d\Omega}\right)_{bac}$$

is the absolute differential Raman cross section of the bacteria in $CM^2$/ bacteria - steradian $$\left(\frac{d\sigma}{d\Omega}\right)_{std}$$

is the absolute differential Raman cross section of the internal standard, $SO_4^{-2} = 5.8 \times 10^{-28}$ cm$^2$/molecule - steradian at 222 nm excitation $I_{bac}, I_{std}$ are the intensities, heights or areas, of the bacterial or standard Raman vibrational band
$E(\upsilon_{laser} - \upsilon_{bac})$ is the efficiency of the monochrometer and detector system at the bacterial Raman scattering frequency.
$E(\upsilon_{laser} - \upsilon_{std})$ is the efficiency of the monochrometer and detector system at the standard Raman scattering frequency
$C_{std}, C_{bac}$ is the molar concentration of the standard and bacteria
L(std) is the local field correction at the standard scattering frequency of the standard solution $$= \left(\frac{n_{std}}{n'_{std}}\right)^2 \frac{(n_{std}^2 + 2)^2 ((n'_{std})^2 + 2)^2}{81}$$

L(bac+std) is the local field correction at the standard scattering frequency of the solution of bacteria+standard $$= \left(\frac{n_{bac+std}}{n'_{bac+std}}\right)^2 \frac{(n_{bac+std}^2 + 2)^2 ((n'_{bac+std})^2 + 2)^2}{81}$$

$$\left(\frac{n_{std}}{n_{bac+std}}\right)^2$$

is the correction for the solid angle of collection of Raman collection optics
(Self - Abs) is the self-absorption correction factor, depends upon the concentration and electronic absorption spectrum of the bacterial+standard solution
$\upsilon_{laser}$ is the frequency of the excitation beam, in wavenumbers
$\upsilon_{bac}$ is the frequency of the bacterial Raman scattering band, in wavenumbers
$\upsilon_{std}$ is the frequency of the standard scattering band, in wavenumbers
$n_{std}$ is the index of refraction of the standard solution at ($\upsilon_{laser} - \upsilon_{std}$)
$n'_{std}$ is the index of refraction of the standard solution at $\upsilon_{laser}$
$n_{bac+std}$ is the index of refration of the bacterial+standard solution at ($\upsilon_{laser} - \upsilon_{std}$)
$n'_{bac+std}$ is the index of refraction of the bacterial+standard solution at $\upsilon_{laser}$

LOCAL FIELD AND SOLID ANGLE OF COLLECTION CORRECTIONS

Equation 2 expresses in mathematical formalism, the factors necessary to calculate the absolute differential Raman cross-section (ADRCS) depicted in FIG. 1. Equation 2 gives the solution independent cross-section of the analyte Raman bands, the cross-section of an isolated bacterium, out of solution, in the gas phase. This is accomplished by the inclusion of two factors in equation 2, the local field correction, and the solid angle correction. The local field correction 32 effectively removes the dependence of the strength of the electronic transition on solvent dielectric constant that affect the intensity of the Raman vibrational transitions. The solid angle correction 35, removes the solvent dependency of the solid angle of Raman light 27 collected with a given collection geometry. As the index of refraction of the bacteria-Raman intensity standard solution increases, the solid angle of Raman light 27 collected decreases. The solid angle of correction factor compensates for this effect. Both of these factors require knowledge of the indexes of refraction at the internal standard scattering frequency for the bacteria+Raman intensity standard solution and the Raman intensity standard solution, however these values are not known. If the Raman cross-sections of the bacteria are reported as values for the bacteria in the buffer used, and the index of refraction of the bacteria-Raman intensity standard solution does not differ significantly from the standard solution alone, the local field and solid angle correction 32, 35 can safely be neglected.

SELF-ABSORPTION CORRECTION

The self-absorption correction 34 depicted in FIG. 1 must be considered to calculate the absolute differential Raman cross-section (ADRCS) according to equation 2. This correction factor 34 accounts of the absorption of the Raman light 27 by the sample. This factor is important when there are significant differences between the electronic absorption of the solution being irradiated at the laser excitation, the Raman intensity standard, and bacterial scattering frequencies. For the bacterial spectra, these frequencies usually span no more than 1700 cm-1. When measuring the electronic absorption spectrum of a turbid sample such as a bacterial suspension, Rayleigh (elastically scattered) light must be rejected. When bacteria are mixed with beef menstrua that comprises blood and muscle cells, fecal material, and other biomatter, the acquisition of the electronic absorption spectrum is further complicated by these additional scatters. For these reasons, special diffuse absorption apparatus or heads-on detectors are needed to minimize the effects of Rayleigh scattering so that an accurate absorption spectra can be obtained and applied to calculate the Raman cross-sections according to equation 2. However, with such a heterogeneous solution as beef menstrua and bacteria, the electronic absorption isn't expected to vary significantly in any given 1700 cm-1 interval between 200 and 300 nm. If this is true, the self-absorption correction factor can safely be neglected.

INSTRUMENT EFFICIENCY CORRECTION

The last correction factor 36 depicted in FIG. 1 necessary to calculate the absolute differential cross-section is the instrument efficiency correction 36. The efficiency of the monochrometer 59 system was measured not to vary more than 3% between 981 and 1700 cm-1 when exciting at 222 nm. Associated with the instrument efficiency correction 36, is the non-linearity of the response of the IPDA detector 36 across the length of the IPDA chip for a given photon flux and wavelength. This amounts to a detector efficiency correction. This non-linearity was corrected for by applying a gain curve correction. After the gain curve correction was applied for the detector 23, the efficiency of the monochrometer-detector system in equation 2 is given by:

$$\frac{E(\tilde{v}_{laser} - \tilde{v}_{bac})}{E(\tilde{v}_{laser} - \tilde{v}_{std})} = 1$$

EQUATION USED TO CALCULATE THE ABSOLUTE RAMAN CROSS-SECTION

The equation used to calculate the absolute differential Raman cross-section depicted in FIG. 1 is calculated in the following manner. Given that efficiency factor is 1, and the neglect of the local field 32, solid angle 35, and self-absorption 34 corrections, the cross-sections of BT and PF are calculated with the following revised equation:

$$\left(\frac{d\sigma}{d\Omega}\right)_{bac} = \left(\frac{d\sigma}{d\Omega}\right)_{std} \frac{I_{bac}}{I_{std}} \frac{C_{std}}{C_{bac}} \quad \text{Equation 3}$$

OPERATION

EXAMPLE I

Bacteria in H20

The Raman system depicted in FIG. 2 with intensified photodiode array (IPDA) detection was used to detect the sample Raman light 12, the gate width was set to 150 ns, the delay time was 500 ns, the repetition rate of the laser was typically 200 Hz. The spectra were produced by the addition of 25 60 second exposures of the detector. The concentration for BT and PF were estimated from their optical densities measured at 600 nm to be in the range of 2–50 million bacteria/ml.

Figure 7:
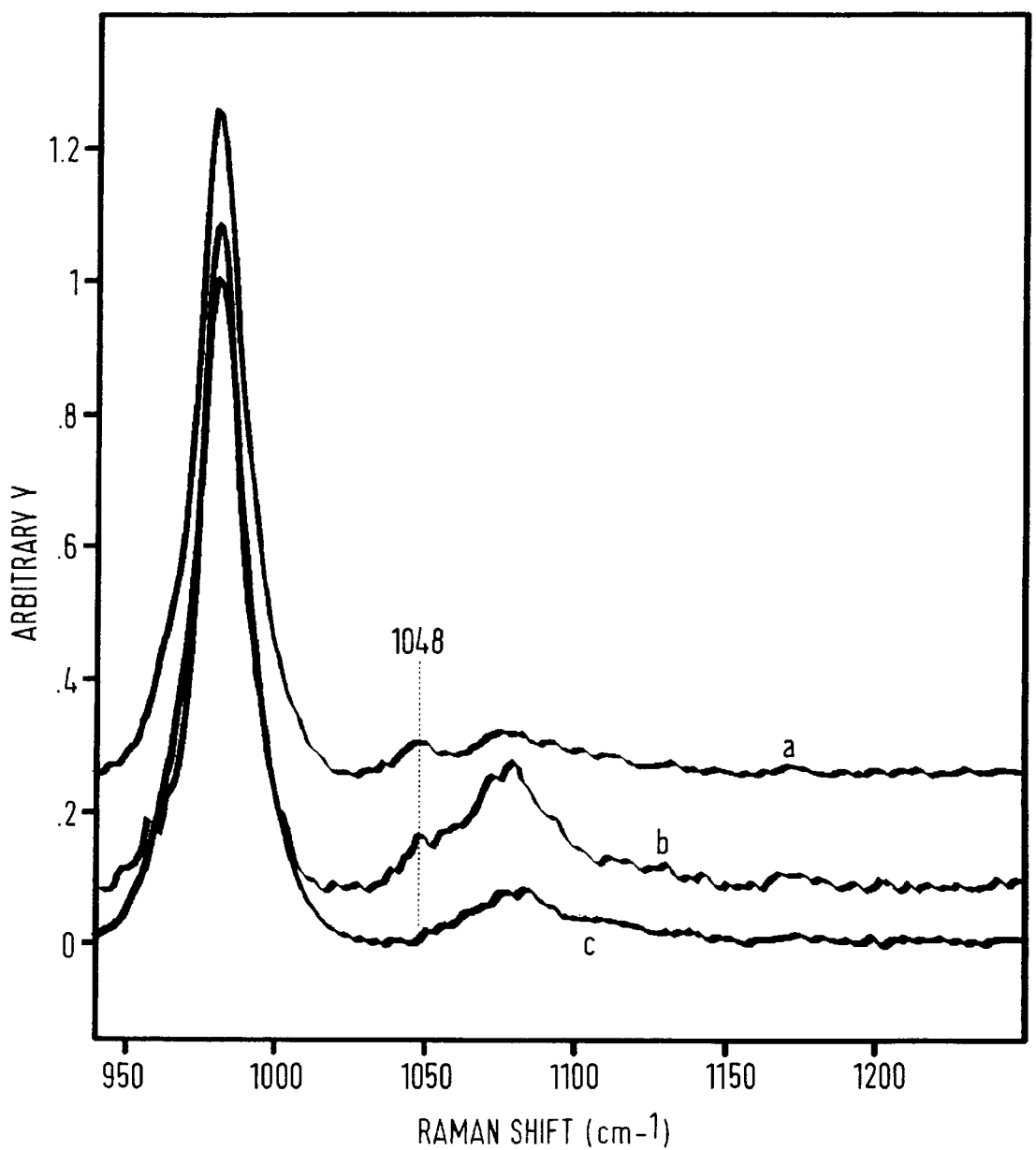
FIG. 7 is a representation of the measured total intensity spectrum at 222 nm excitation spectra of (a) Brocothrix Thermospacta (BT) in water buffer, (b) Pseudomonas fluorescens (PF) in water buffer, and (c) water buffer. The ordinate is normalized to the height of the 981 cm-1 SO4-2 band in each spectrum and the abscissa scale is Raman shift, cm-1. This representation shows the 981 cm-1 SO4-2 absolute Raman intensity in each solution and the 1048 cm-1 bacterial Raman band of (a) BT and (b) PF is not present in the (c) water buffer.

FIG. 7 shows the 222 nm excitation spectra of (a) BT in water buffer, (b) PF in water buffer, and (c) water buffer. The only band that can be unambiguously assigned to bacterial scattering is the 1048 cm-1 band for both BT and PF. The BT band is much broader than the PF band centered at 1048 cm-1.

EXAMPLE II

Figure 8:
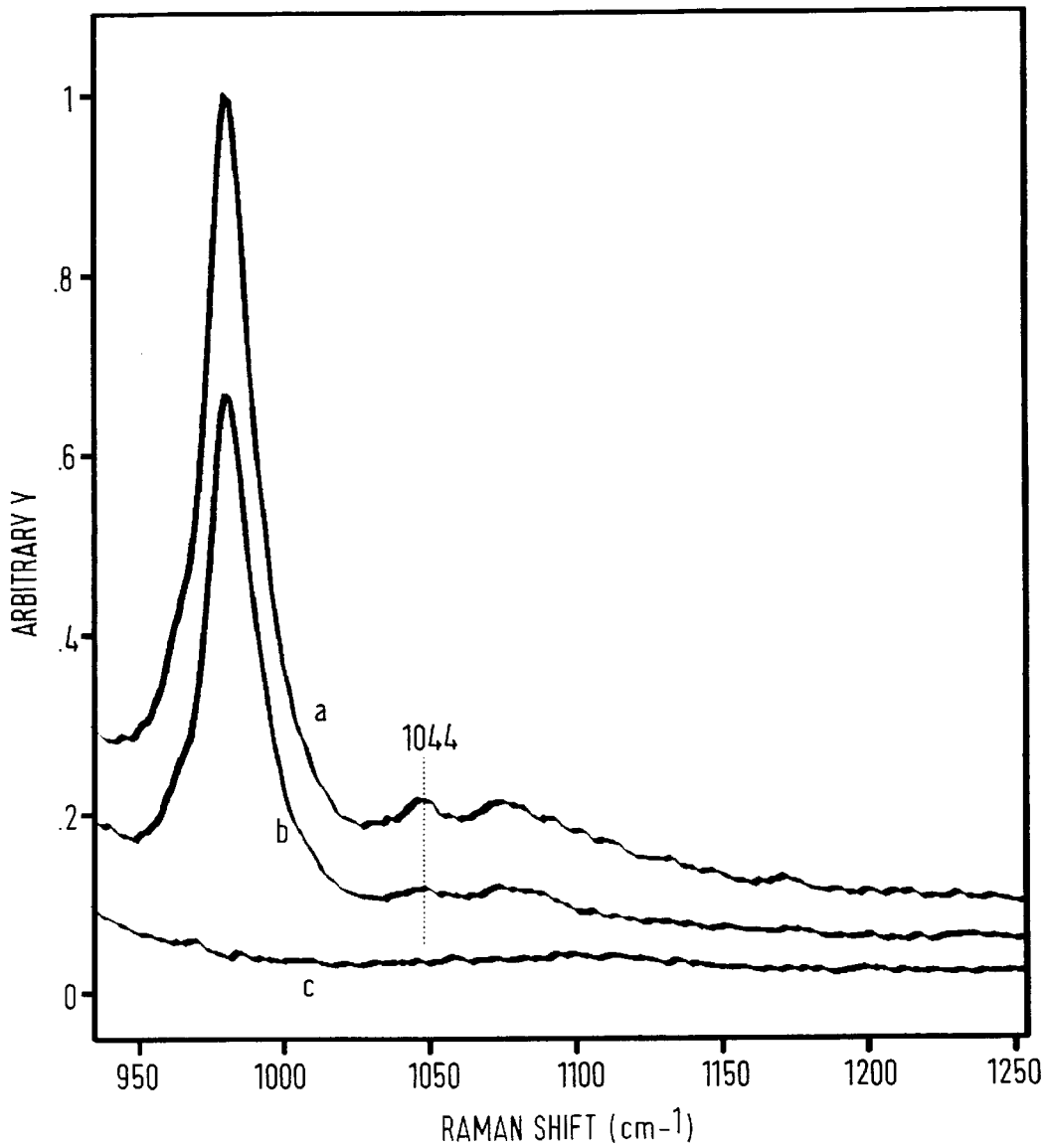
FIG. 8 is a representation of the polarization components of the Raman spectrum of BT at 222 nm excitation, the ordinate is normalized to the height of the 981 cm-1 SO4-2 band in the measured total intensity spectrum and the abscissa scale is Raman shift, cm-1. The polarization components of BT shown are (a) the measured total intensity, (b) the measured parallel component, and (c) the calculated corrected perpendicular component. This representation shows that there is negligible intensity in perpendicular component of the 1048 cm-1 band of BT so that the depolarization ratio of the 1048 cm-1 of BT at 222 nm excitation is 0.

Depolarization Ratio of the 1048 cm-1 band of BT. The Raman system depicted in FIG. 2 with intensified photodiode array (IPDA) detection was used to detect the Raman light 27, the gate width was set to 150 ns, the delay time was 500 ns, the repetition rate of the laser was typically 200 Hz. The spectra were produced by the addition of 25 60 second exposures of the detector. FIG. 8 shows the (a) measured total intensity, (b) parallel, and (c) corrected perpendicular component spectra of BT at 222 mn excitation. Since there is no detectable intensity in the perpendicular component in the 1048 cm-1 band, its depolarization ratio is very close to 0.

EXAMPLE III

Effects Of Hydrogen-Deuterium Exchange On The Resonance Raman Spectra of BT and PF The Raman system 1 depicted in FIG. 1 with intensified photodiode array (IPDA) detection was used to detect the sample Raman light 12, the gate width was set to 150 ns, the delay time was 500 ns, the repetition rate of the laser was typically 200 Hz. The spectra were produced by the addition of 25 60 second exposures of the detector.

Figure 9:
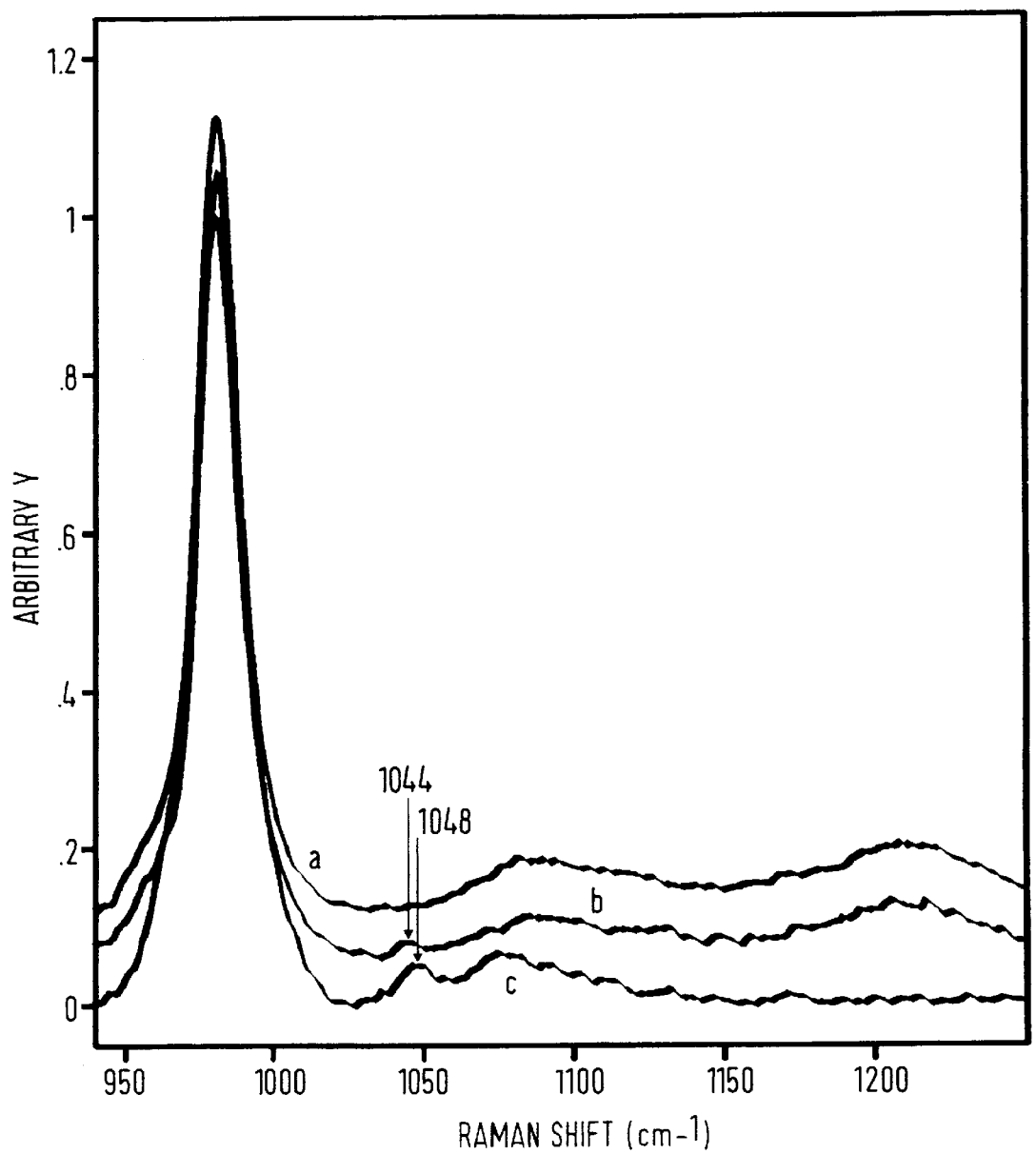
FIG. 9 is a representation of resonance Raman spectra of BT at 222 nm excitation subjected to hydrogen-deuterium (H-D) exchange over different time intervals, the ordinate for each spectrum is normalized to the height of the 981 cm-1 SO4-2 band and the abscissa scale is Raman shift, cm-1. The spectra shown are (a) BT subjected to 0.3 hours of H-D exchange in D20 buffer, (b) BT subjected to 9.8 hours of H-D exchange in D20 buffer, and (c) BT in H20 buffer. These spectra show the sensitivity of the 1048 cm-1 band of BT in H20 buffer to the effects of hydrogen-deuterium (H-D) exchange, this band disappears after 0.3 hours of H-D exchange and a new band appears at 1044 cm-1 after 9.8 hours of H-D exchange.

FIG. 9 shows the sensitivity of the resonance Raman spectrum of BT to the effects of hydrogen-deuterium (H-D) exchange. Changes in the resonance Raman spectra of BT are observed when 2.0 ml of stock BT solution are mixed with 10.0 ml of 0.15 M Na2SO4, 0.20 M Na2HPO4, pD 7.25 in heavy water (D20). The BT stock was quickly mixed with the buffer and the resonance Raman spectrum (a) was collected with a 25 minute integration time. The BT band at 1048 cm-1 observed in H20 buffer, is not present in this spectrum. The solution was allowed to sit at room temperature for 9.5 hours, after which the spectrum (b) was collected. We observe a band in the new position of 1044 cm-1 not present in the spectrum collected after (a) 25 minutes of exchange, nor present in the (c) H20 solution.

Figure 10:
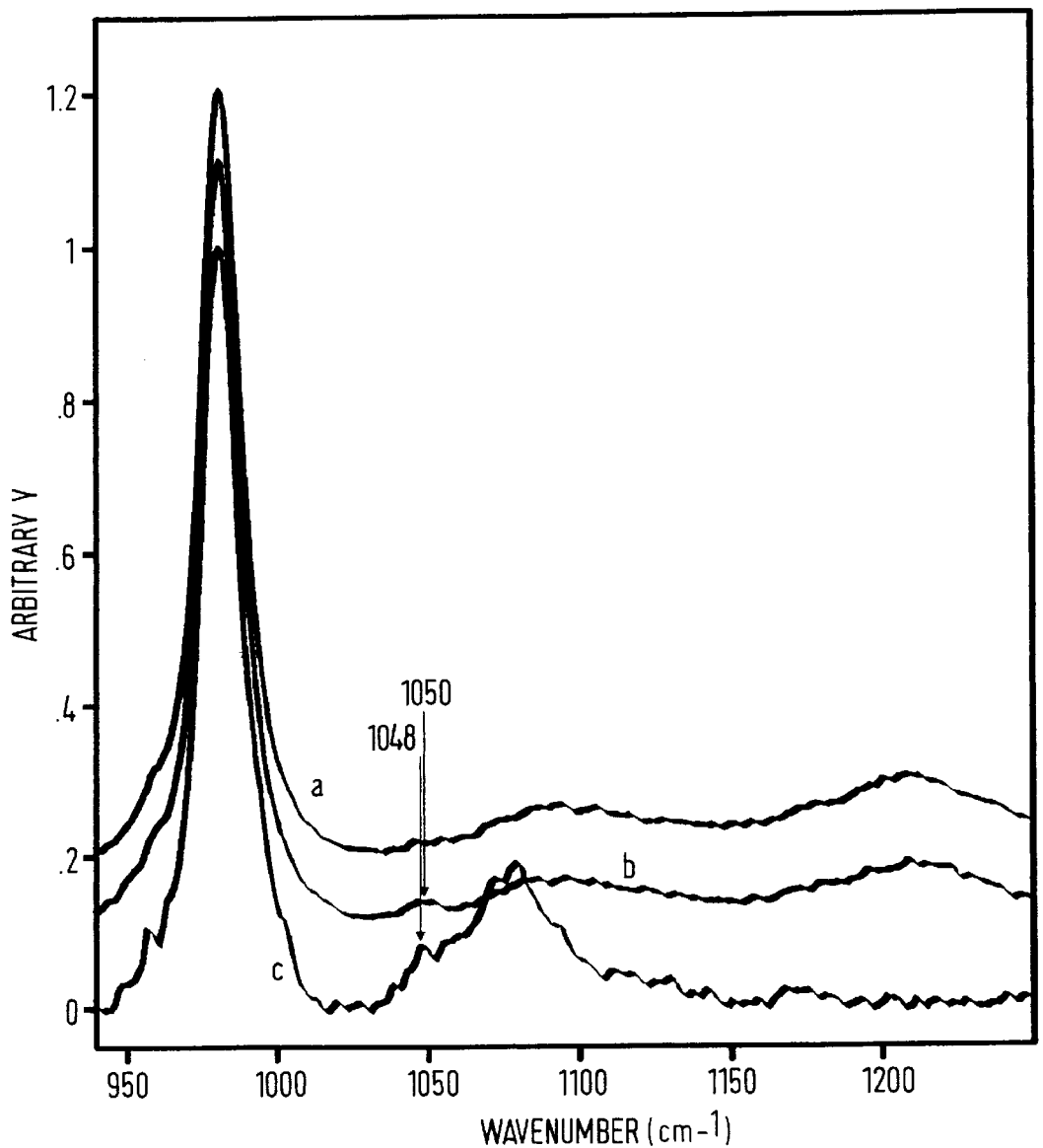
FIG. 10 is a representation of resonance Raman spectra of PF at 222 nm excitation subjected to hydrogen-deuterium (H-D) exchange over different time intervals, the ordinate for each spectrum is normalized to the height of the 981 cm-1 SO4-2 band and the abscissa scale is Raman shift, cm-1. The spectra shown are (a) PF subjected to 0.3 hours of H-D exchange in D20 buffer, (b) PF subjected to 9.8 hours of H-D exchange in D20 buffer, and (c) PF in H20 buffer. These spectra show the sensitivity of the 1048 cm-1 band of PF in H20 buffer to the effects of hydrogen-deuterium (H-D) exchange, this band disappears after 0.3 hours of H-D exchange and new band appears at 1050 cm-1 after 9.8 hours of H-D exchange.

FIG. 10 shows the sensitivity of the resonance Raman spectrum of PF to the effects of hydrogen-deuterium (H-D) exchange. Changes in the resonance Raman spectra of PF are observed when 2.0 ml of stock PF solution are mixed with 10.0 ml of 0.15 M Na2SO4, 0.20 M Na2HPO4, pD 7.25 in heavy water (D20). The PF stock was quickly mixed with the buffer and the resonance Raman spectrum (a) was collected with a 25 minute integration time. The PF band at 1048 cm-1 observed in H20 buffer, is not present in this spectrum. The solution was allowed to sit at room temperature for 9.5 hours, after which the spectrum (b) was recollected. We observe a band in the new position of 1048 cm-1 not present in the spectrum collected after (a) 25 minutes of exchange nor present in the (c) H2O solution.

Figure 11:
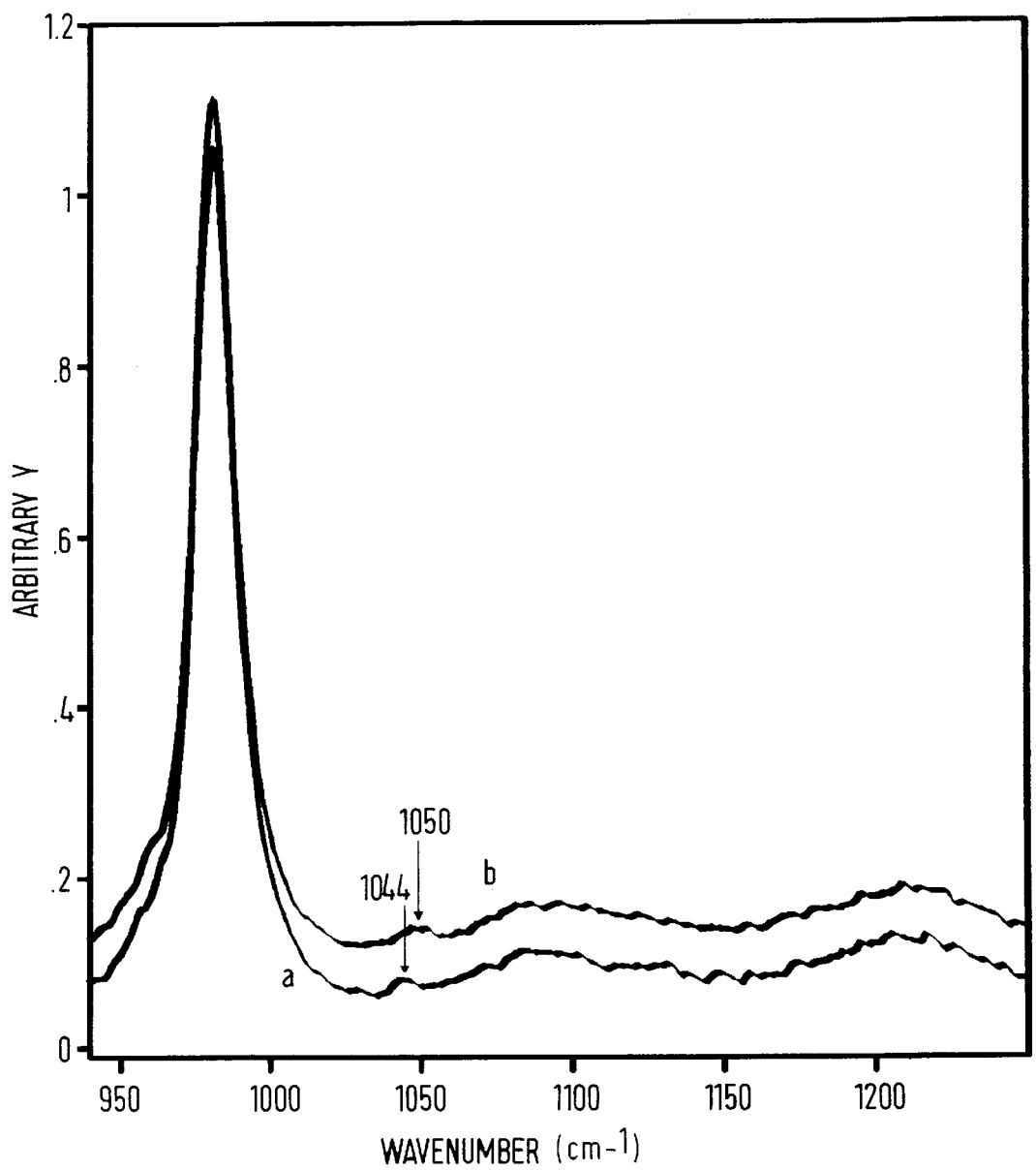
FIG. 11 is a representation of the 222 nm excitation resonance Raman spectra of (a) BT and (b) PF that have subjected to 9.5 hours of (H-D) exchange, the ordinate for each spectrum is normalized to the height of the 981 cm-1 SO4-2 band and the abscissa scale is Raman shift, cm-1. This representation shows that the frequency of the bacterial Raman band of BT and PF shift in different directions as a result of H-D exchange

FIG. 11 shows the resonance Raman spectra of (a) BT and (b) PF that have subjected to 9.5 hours of (H-D) exchange. We observe that after exchange the 1048 cm-1, the band initially disappears, but a new band reappears for both BT and PF. The new band reappears at the lower frequency of 1044 cm-1 for BT and at the higher frequency of 1050 cm-1 for PF. The data in FIGS. 9, 10 and 11 show that the 222 nm excitation resonance Raman spectra of BT and PF can be used to distinguish between these to species if these bacteria are subjected to H-D exchange. The H-D exchange process causes the 1044 cm-1 band that both species exhibit to shift their wavenumber position in different directions, as well as modulating the intensities of these bands as a function of time. The absolute differential Raman cross-sections of BT and PF are given in the table below. These observations form the bases for the identification and quantification of bacteria.

TABLE 1

Absolute Differential Raman Cross-Sections of Bacteria Brocothrix Thermospacta and Pseudomonas Fluorescens, 222 nm laser excitation Height of the SO4-2 981 cm-1 band = 1.00
2–50 x 10^6 bacteria/ml

| Bacterium | H-D Exchange time (Hours) | Frequency cm$^{-1}$ | Height | Cross Section, cm$^2$/ (bacteria-steradian) |
|---|---|---|---|---|
| BT (H$_2$O) | — | 1048 | 0.027 | 1.2–30 × 10$^{-17}$ |
| BT (D$_2$O) | .3 | 1044 | 0 | 0 |
| BT (D$_2$O) | 9.8 | 1044 | 0.014 | 0.60–15 × 10$^{-17}$ |
| PF (H$_2$O) | — | 1048 | 0.030 | 1.3–33 × 10$^{-17}$ |
| PF (D$_2$O) | .3 | 1050 | 0 | 0 |
| PF (D$_2$O) | 9.8 | 1050 | 0.013 | 0.56–14 × 10$^{-17}$ |

EXAMPLE IV

EFFECTS OF HYDROGEN-DEUTERIUM EXCHANGE ON THE RESONANCE RAMAN SPECTRA OF THE BEEF MENSTRUA-BACTERIA SOLUTION

Figure 12:
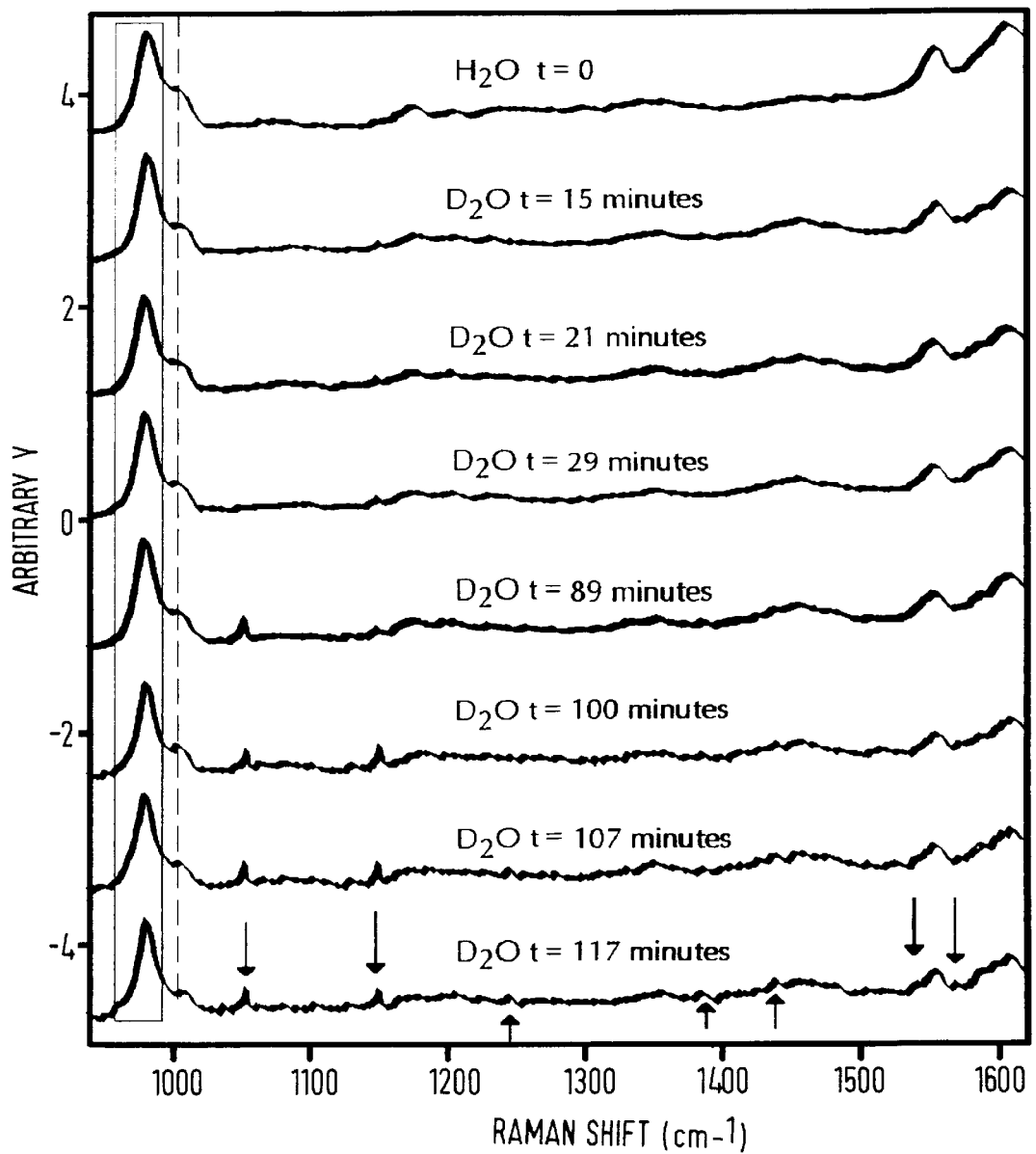
FIG. 12 is a representation of the 222 nm excitation resonance Raman spectra of beef menstrua-bacteria solution, the ordinate for each spectrum is normalized to the height of the 981 cm-1 S4-2 band and the abscissa scale is Raman shift, cm-1. The topmost spectrum is beef menstrua-bacteria solution in H20 buffer, below are the spectra acquired 15, 21, 29, 89, 100, 107, and 117 minutes after mixing the beef menstrua with the D20 buffer. This representation shows the time dependent effects of H-D exchange on the beef menstrua-bacteria solution.

The Raman system using the intensified charge couple device (ICCD) detection was used to detect the Raman light 27, the repetition rate of the laser was typically 200 Hz. The spectra were produced by the addition of 25–50 20 second exposures of the detector. FIG. 12 shows the effects of H-D exchange on the resonance Raman spectra of beef menstrua to which bacteria was added. This sample was prepared by adding 3.3 ml of beef menstrua to 6.7 ml to either the 0.15 M Na2SO4, 0.20 M Na2HPO4, pD 7.25 in heavy water (D20) or 0.15 M Na2SO4, 0.20 M Na2HPO4 pH 7.25 in water (H20). The total bacteria concentration is 24,000 bacteria/ml estimated from an ATPase activity test. The bacteria were a mixture of bacteria that are found on beef carcasses. The beef menstrua-bacteria solution was observed to contain bone and tissue fragments and was opaque with red cow blood. The rectangular box on the left encompasses the 981 cm-1 mode of the internal standard, SO4-2. The uppermost spectrum in FIG. 12 is that of beef menstrua-bacteria in the H2O based buffer. This spectrum serves as the reference spectrum to judge the effects of H-D exchange on the sample. The spectra below this spectrum show the time dependent effects of H-D exchange on the resonance Raman spectra acquired 15, 21, 29, 89, 100, 107, and 117 minutes after mixing the beef menstrua with the D20 buffer. Proceeding from low to high frequency, the following changes are noted in these spectra. The dashed line at 1003 cm-1 indicates the position of a maximum of a band from the beef menstrua-bacteria solution in H20 buffer. This maximum shifts to 1007 cm-1 after 117 minutes of H-D exchange. There is a continuous decrease in the height of this band relative to the height of the sulfate standard at 981 cm-1 as the H-D exchange process proceeds. A new band at 1054 cm-1, not present in the H2O based buffer, acquires significant intensity in the D20 buffer. Similarly, a very weak band in the H2O buffer at 1151 cm-1, also grows significantly in intensity as a result of the H-D exchange process. New bands present in the 117 minute D20 spectrum not present in the H2O spectrum are found at 1247, 1387, 1441, 1544, 1572 cm-1. These bands can also be found in spectra acquired in the D20 buffer earlier. Since all spectra are normalized to the height of the sulfate standard at 981 cm-1, the height of each band is equivalent to the ratio of the height of each band to the height of the sulfate band that serves as the internal intensity standard. The spectra presented in this format, allow us to follow both relative (between successive Raman spectra) and absolute (relative to the sulfate height or area) changes in the Raman spectra. These observations forms the basis for the third step in FIG. 1, the identification and quantification of bacteria.

Figure 13:
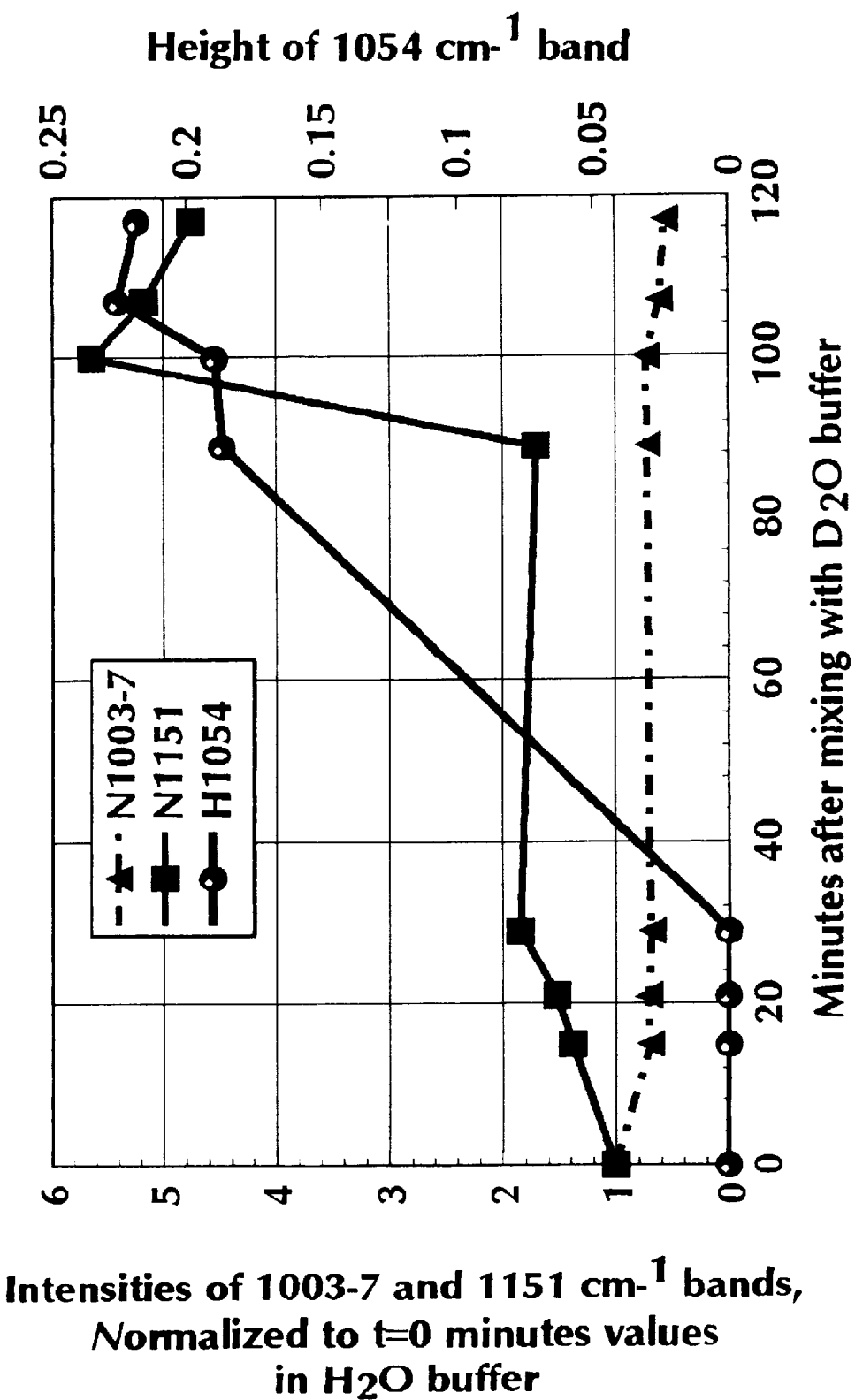
FIG. 13 is a representation of the time dependent H-D exchange effects on the heights of some of the Raman bands of the beef menstrua-bacteria solution acquired with 222 nm excitation. The ordinate for the changes in the 1003-7 and 1151 cm-1 bands normalized to their values in H20 buffer is shown on the left side of the graph, the ordinate for the height of the 1054 cm-1 band is shown on the right side of the graph, while the abscissa is duration of H-D exchange in minutes. This representation shows that the heights if these Raman bands change at different rates.

FIG. 13 summarizes some of the changes in the time dependent behavior of the resonance Raman spectra of the beef menstrua-bacteria in D20 buffer. The heights of the 1003-7 and 1147 cm-1 bands, normalized to their values in H20 buffer, are plotted as a function of time. Also shown in this graph is the change height of the 1051 cm-1 as a function of time. This figure is unambiguously shows that these H-D exchange induced changes in the heights of the Raman bands, relative to the absolute Raman cross-section standard, occur at different rates. These observations form the basis for the identification and quantification of bacteria.

Figure 14:
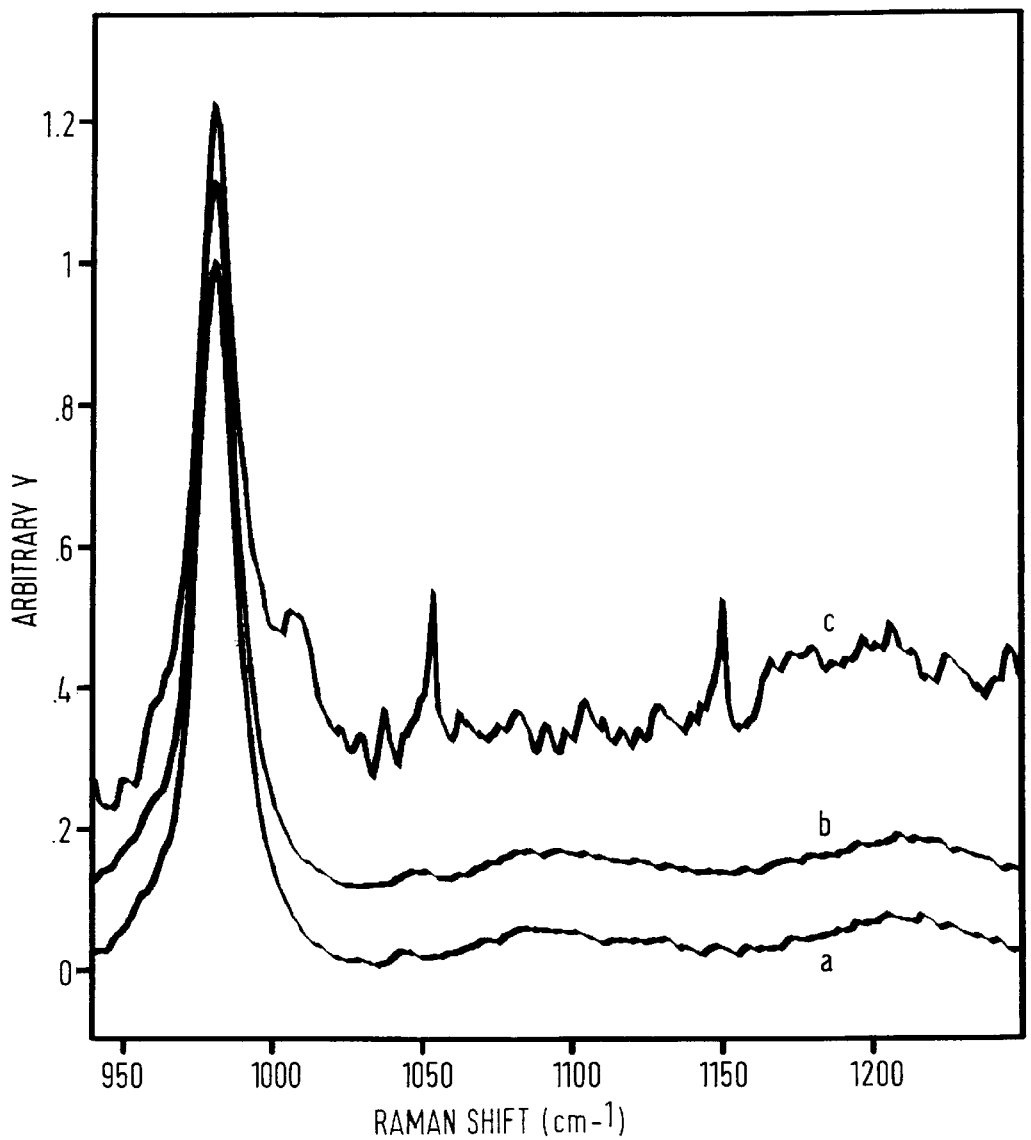
FIG. 14 is a representation of the resonance Raman spectra of (a) BT after 9.8 hours of H-D exchange, (b) PF after 9.8 hours of H-D exchange, and beef menstrua-bacteria after 1.95 hours of H-D exchange at 222 nm excitation. The ordinate is normalized to the height of the 981 cm-1 SO4-2 band in each spectrum and the abscissa scale is Raman shift, cm-1.

FIG. 14 shows the spectra of the beef menstrua-bacteria, PF, and BT samples in D20 buffer. The dashed line indicates the position of the vibrational band associated with the BT bacteria at 1048 cm-1 , as well as its position relative to the PF band at 1043 cm-1, and a beef menstrua-bacteria band at 1054 cm-1. These three bands are present at these positions only when the samples are subjected to H-D exchange.

RAMIFICATIONS AND SCOPE

FIG. 1 depicts a novel and nonobvious bacterial identification and quantification system using resonance Raman spectroscopy that provides quantitative information, that is instrument independent, requires no special sample preparation, reduces spectral artifacts, that has the potential of discriminating between pathogenic and non-pathogenic bacteria, provides data faster than classical bacteriological test, and is economical per test.

RAMAN SPECTRAL BACTERIAL TITER: ABSOLUTE DIFFERENTIAL RAMAN CROSS-SECTIONS OF BACTERIA

The determination of the differential Raman cross-sections of bacteria as depicted in FIG. 1, and extracted from the data in FIGS. 7, 9, and 10 using equation 3, and summarized in Table 1, are first described in this invention. This establishes a resonance Raman spectral titer for these bacteria in the specific buffer used. From the cross-section values reported above, and the relative heights of sulfate to bacterial Raman bands, one can use equation 3 to calculate the number of bacteria/ml in the sample.

From the cross-section values reported above, the sulfate absolute differential Raman cross-section standard, and the relative heights of sulfate to bacterial Raman bands, one uses equation 3 to solve for Cbact, the number of bacteria/ml in the sample.

Using equation 3, the absolute differential Raman cross-sections of these Raman bands is calculated once the concentration of the species responsible for the appearance of these vibrational bands is determined.

RAMAN SPECTRA OF BACTERIA AND BEEF MENSTRUA ARE SENSITIVE TO ENVIRONMENTAL PERTURBATIONS EFFECTS OF H-D EXCHANGE ON THE RAMAN SPECTRA OF BACTERIA

The relationship depicted in FIG. 1 between absolute differential Raman cross-sections of bacteria and environmental perturbations is understood by considering the data in FIGS. 9 and 10 and Table 1. The following conclusion can be drawn for the Raman bands observed for BT and PF in the buffers used: their absolute differential Raman cross-sections are different in D20 than H2O buffer, that their absolute differential Raman cross-sections in D20 change as a function of H-D exchange time, and that the BT and PF Raman bands shift their frequency in different directions upon H-D exchange. Because all bacteria are comprised of proteins, fats, and nucleic acids, it is reasonable to expect all bacteria to exhibit time dependent changes in the intensity and frequency of some of their vibrational bands in their resonance Raman spectra when undergoing H-D exchange, and excited at the appropriate excitation frequency. These observations and conclusions form the basis of the claim that enviromnental perturbations, in the form of H-D exchange induced changes in the absolute differential Raman cross-sections of the vibrational bands of bacteria, facilitate the identification and quantification of bacteria.

H-D Exchange and Raman Spectroscopy

The gist of the idea is to combine the spectral selectivity of resonance Raman spectroscopy and the physical-chemical selectivity of H-D exchange. These two selection mechanisms allow us to preferentially observe and change the vibrational bands associated with proteins and nucleic acid constituents. H-D exchange affords selectivity, via manipulation of external physico-chemical parameters, to control the nucleic acid: nucleotide to protein relative exchange rates, and thereby the relative extent of nucleic acid: nucleotide and protein deuteration. The deuteration and the extent of deuteration can be observed with Raman spectroscopy. By choosing the appropriate excitation frequency, either nucleic acids or proteins are preferentially enhanced.

This manipulation of H-D exchange rate and excitation frequency will be very useful in establishing the identity of the constituents in a heterogeneous sample containing different components, i.e. different types of bacteria. Let's assume that the spectra of two bacterial species are very similar at a given excitation frequency. We can subject the sample containing the two bacterial species to H-D exchange under conditions such that their spectra change in different, predetermined ways. This will facilitate the identification and quantitation of the bacteria and analytes in question, and would not be possible with the static, non-H-D exchange picture.

EFFECTS OF H-D EXCHANGE ON THE RAMAN SPECTRA OF BEEF MENSTRUA-BACTERIA SOLUTION

The relationship between the absolute differential Raman cross-sections of beef enstrua-bacteria and environmental perturbations is understood by considering the data in FIGS. 13 and 14. FIG. 13 shows that the heights of the Raman bands of the beef menstrua-bacteria solution (relative to an absolute Raman cross-section standard) change at different rates as a function of H-D exchange time. Using equation 3, the absolute differential Raman cross-sections of these Raman bands can be calculated once the concentration of the species responsible for the appearance of these vibrational bands is determined. The following conclusion can be drawn for the beef menstrua-bacteria sample: the absolute differential Raman cross-sections of some of its vibrational bands are different in D2O than H2O buffer, that some of these absolute differential Raman cross-sections in D2O change as a function of H-D exchange time, and that some of these Raman bands shift their frequency upon H-D exchange. The H-D exchange induced changes in the absolute differential Raman cross-sections observed in the resonance Raman spectra of the mixture of bacterial species and beef menstrua, exhibit the expected time dependent behavior of biomolecules with exchangeable protons that have different accessibility to solvent. Some of the Raman bands in the spectrum of the bacteria-menstrua mixture probably belong to bacteria, and some to extra-bacterial biomolecular constituents of the beef menstrua. The time dependent changes in the Raman spectra of a bacteria-free beef menstrua solution, with respect to an internal standard, would be useful in identification of the characteristic Raman band profiles or "spectral signatures" of the extra-bacterial components. These observations and conclusions form the basis of the claim that environmental perturbations, in the form of H-D exchange induced changes in the absolute differential Raman cross-sections of the vibrational bands of a beef menstrua-bacteria solution, facilitate the identification and quantification of the bacteria in beef menstrua.

FIG. 14 compares the (a) BT, (b) PF, and (c) beef menstrua-bacteria resonance Raman spectra, it is observed that all samples exhibit a band in the 1049+/−5 cm-1 region that is sensitive to the H-D exchange time. Whether or not this band observed in the beef menstrua-bacteria solution is indeed a bacterial vibrational band, the Raman spectra of each of the bacteria species has to be individually collected, and their spectra compared to the spectra obtained from the beef menstrua-bacteria solution.

DEPOLARIZATION RATIO OF BACTERIAL RAMAN BANDS

Figure 15:
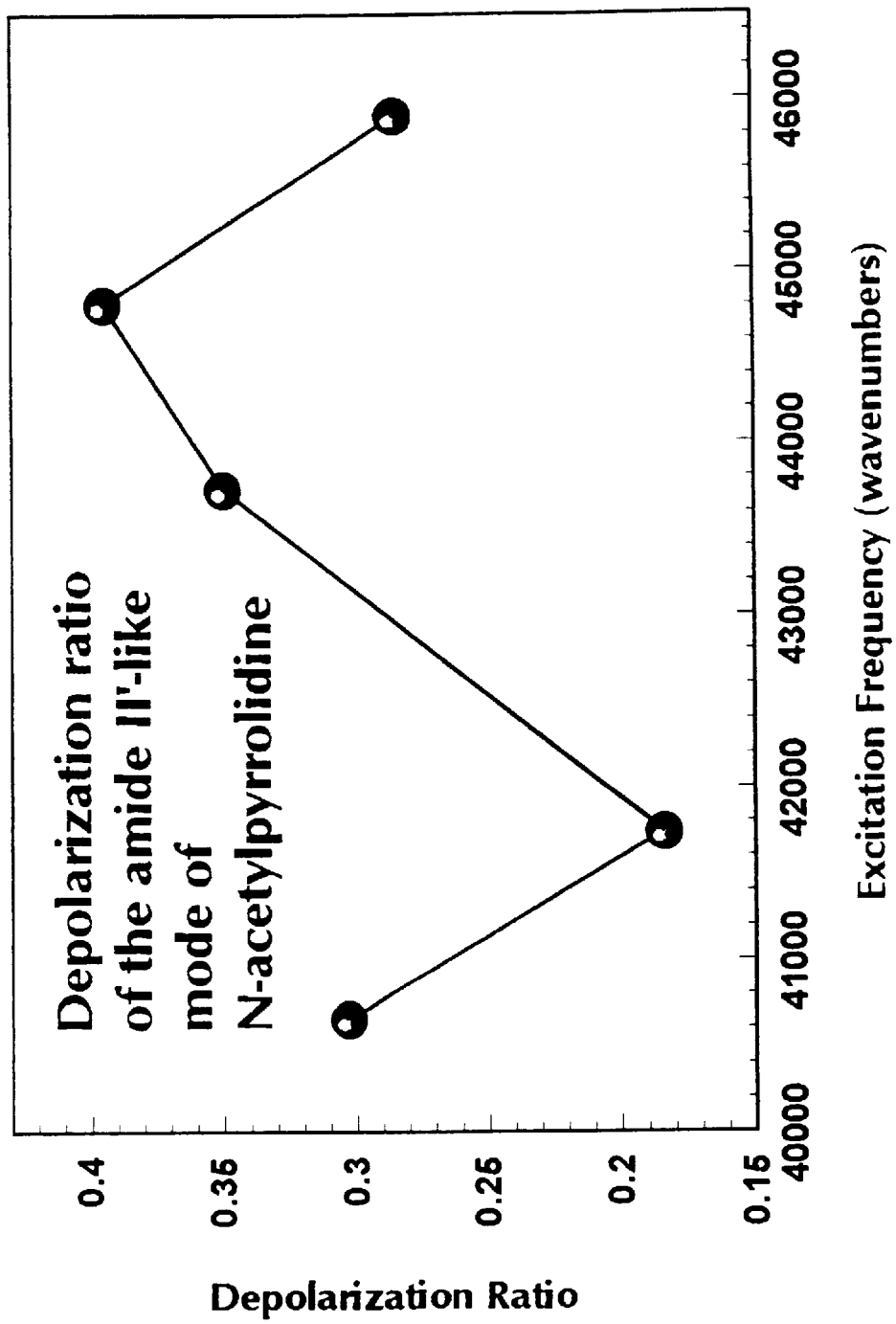
FIG. 15 is a graph of depolarization ration as a function of excitation frequency.

The depolarization ratio of Raman bands may be a taxonomic of a bacterium and extra-bacterial components. A depolarization ratio of 0 has been measured for BT at 1048 cm-1 in the buffer at 222 nm excitation. It has been shown that this observable can vary dramatically with excitation frequency for the peptide bond, this observable is sensitive to the environment and number of excited states and or ground contributing to the resonance Raman scattering process. See FIG. 15.

Gain Curve Correction

A sandblasted quartz plate was placed immediately in front of the detector to act as a light diffuser so as to evenly expose the detector. A deuterium lamp, 0.5 m from the detector, generated UV light that was filtered through a band pass filter 300+/−15 nm (I have to look up this number to make sure) exposing the detector. Detector parameters we set to be identical to those used during the collection of Raman data, with the exception of total exposure time. The total exposure time was set so as to bring the collected counts for a single scan to be approximately 14,000. One thousand scans of the UV lamp were signal averaged to produce a measured gain curve spectrum while one thousand dark current scans were signal average to produce dark current spectrum. The dark current spectrum was subtracted from the measured gain curve spectrum, with both regions on the edge of the detector not intensified truncated away to produce a calculated gain curve spectrum. The calculated gain curve spectrum was divided by the count reading at pixel 512, to produce a final gain curve correction spectrum The observed experimental Raman spectra were divided by the final gain curve spectrum to produce gain curve corrected Raman spectra.

SYSTEM CONSIDERATIONS

SAMPLE HANDLING AND PREPARATION

The introduction of the of the new sampling handling apparatus depicted in FIG. 4 reduces the likelihood that the biomolecules in the sample will denature due to interactions with extensive quartz surfaces found in the quartz capillary tubes previously used, and reduces the likelihood of photo-decomposition of the sample and the quartz in the area that the laser impinges upon. This reduction of the of photode-composition of the sample and elimination of the hotode-composition of the sample container will reduce the likelihood of laser induced spectral artifact. It has been shown with pure cultures of bacteria and mixtures of bacteria with beef menstrua that no special sample preparation is required to acquire resonance Raman spectra.

DEPOLARIZATION AND ABSOLUTE RAMAN CROSS-SECTION STANDARDS

FIG. 1 depicts a bacterial quantification and identification system with which a single absolute Raman intensity standard has been used, the SO4-2 ion. These experiments could be carried out with any absolute differential Raman cross-section standard compatible with the requirements of the bacteria, pH, solubility, ionic strength, etc. Absolute intensity standards have been measured for a number of inorganic and organic species. The use of these species for depolarization ratio standards requires that that this value is known for at least one of the vibrational bands of the Raman standard at the laser excitation frequency used.

The depolarization ratio is sensitive to changes in the excitation frequency, environmental conditions, number of excited states; because of this multiple sensitivity, it is reasonable to expect that the depolarization ratio will facilitate the identification (and possibly the quantification) of bacteria. The depolarization ratio is probably more sensitive to changes in the excitation frequency, environmental conditions, number of excited states than the absolute differential Raman cross-section.

The change in magnitude of this observable as a function of excitation frequency, buffer, H-D exchange time, and other environmental parameters may also facilitate the unique taxonomic identification of bacteria and extra-bacterial components.

ESTIMATED TIME TO ACQUIRE A RESONANCE RAMAN SPECTRUM

The time it takes to acquire Raman data with the spectrometers depends upon the efficiency of the monochrometer and detectors used, and the laser power incident on the sample. Given the efficiency of a state of the art system optimized to acquire resonance Raman spectra, and the use of a continuous wave laser excitation source, at least a 100 fold increase in the data collection speed can be obtained. Although the description above contains many specificities, these should not be construed as limiting the scope of the invention but as merely providing illustrations of some of the presently preferred embodiments of this invention. Various other embodiments and ramifications are possible within it's scope. For example, the following the following ramifications are considered.

NOVEL QUANTITATIVE INFORMATION REQUIRES COMPUTER PROCESSING ALGORITHMS FOR EFFICIENT BACTERIAL ANALYSIS

To efficiently identify and quantify bacteria in samples, the resonance Raman data collected will, by necessity, be analyzed with computerized algorithms utilizing the spectra of known bacteria.

INDUSTRIAL APPLICATION REQUIRES INSTRUMENT INDEPENDENT DATA

Figure 16:
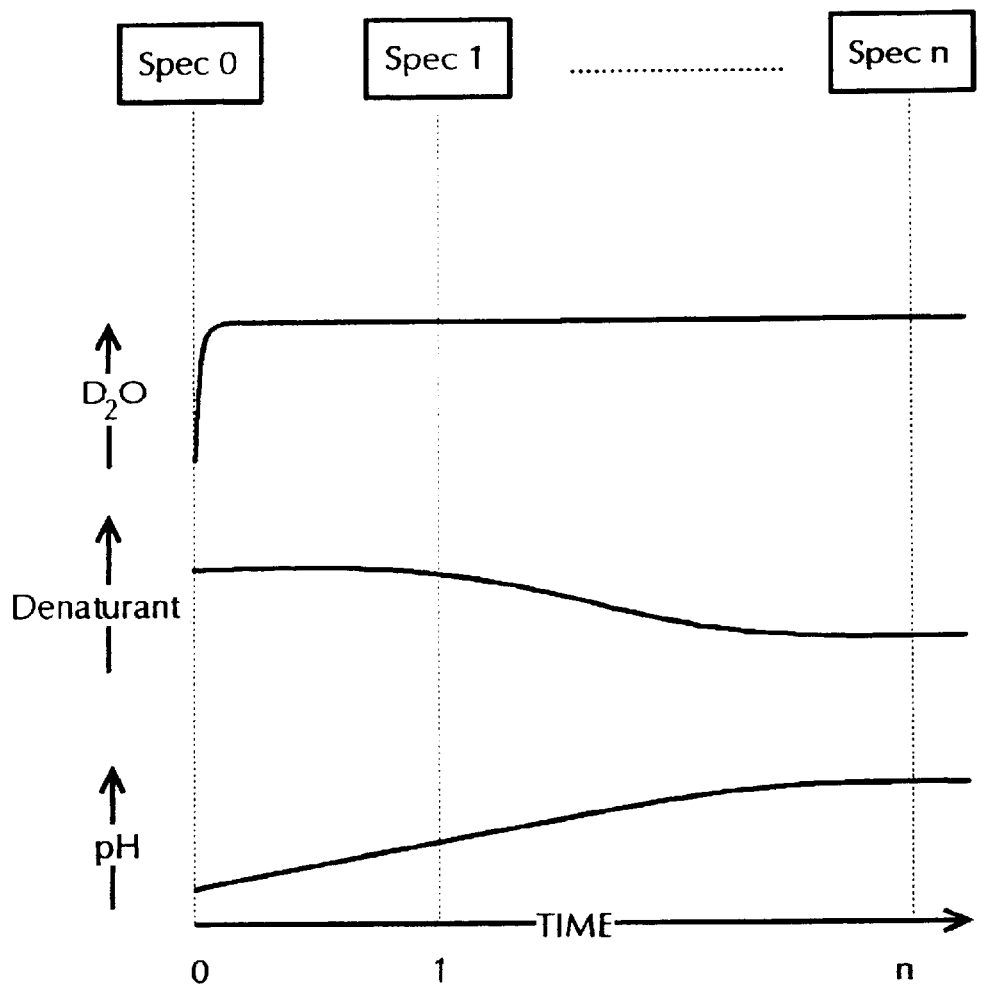
FIG. 16 is a depiction of the method used to collect a Raman response profile.
Figure 17:
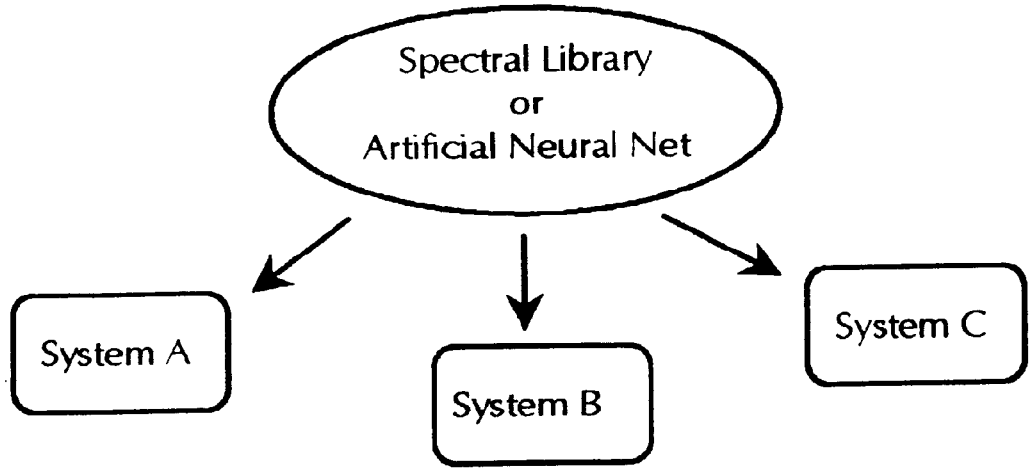
FIG. 17 is a representation of the different regimes of computerized spectral analysis (a) with depolarizer 32 and (b) without depolarizer 32 in the Raman collection optics 35.
Figure 17:
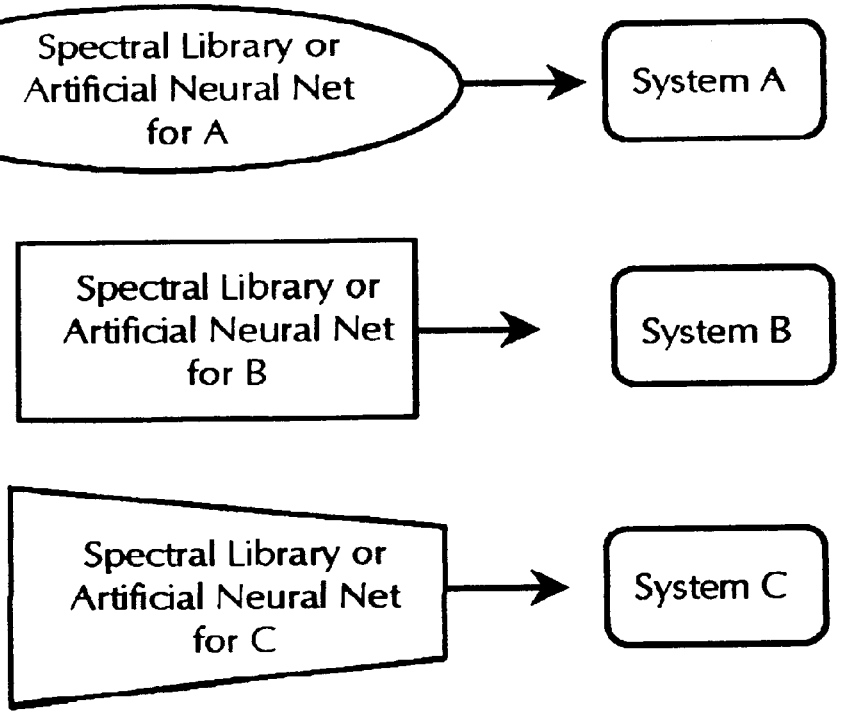

FIG. 16 shows two situations where Raman data is collected from different instruments, (a) using depolarizer 32 in the Raman collection optics 35 and (b) without the depolarizer 32 in the Raman collection optics 35. In situation (a) a single spectral library or artificial neural network can be used to analyze the data from the non-identical Raman spectrometers, whereas in (b), because depolarizer 32 is absent, the data from each of the non-identical Raman spectrometers must be processed with dedicated spectral libraries or artificial neural networks that are specific for each of the Raman spectrometers. With the inclusion of the corrections factors depicted in FIG. 1, and the depolarizer 32 in front of the monochrometer 30 in FIGS. 2 and 3, the information acquired by the Bacterial identification and quantification system is instrument independent, that is, detector, grating, and monochrometer bias has been removed. The critical importance of this feature will become evident upon consideration of the following methods of computerized spectral recognition.

SEQUENTIAL LOOKUP IN DATABASE

These algorithms in their simplest form entail comparing the resonance Raman spectrum or spectra of the sample containing the bacteria to be identified to known spectra of bacteria stored in a spectral database. It is envisioned that the data in this database will be collected by a single Raman spectrometer and that the spectra will be collected at many excitation frequencies for a variety of bacteria. This computerized database will be employed by a plurality of distinct Raman spectrometers for bacterial identification and quantification, each with non-identical detector, grating, and monochrometer biases. The successful identification and quantification of bacteria using this single computer database by a plurality of distinct Raman spectrometers necessitates that the data collected by every Raman spectrometers be instrument independent. If this were not so, a dedicated spectral database would have to be generated for each Raman spectrometer with a specific detector, grating, and monochrometer combination. This would make the identification and quantification of bacteria in an industrial environment impractical. Thus, a single database may be utilized by all Raman spectrometers to identify and quantify bacteria provided that the procedures and designs described in this invention are followed.

ARTIFICIAL NEURAL NETWORKS

Artificial neural network algorithms offer alternatives to the method of identification and quantification of bacteria discussed above, the comparison of the spectrum or spectra of a bacterial sample to the known spectra of bacteria in a database. This method involves time consuming look-ups through the database. Neural networks can be trained to associate a substance to its spectrum through presentation of the known spectra to the neural network using special learning paradigms. Once the artificial neural network has been trained, the spectral recognition process of an unknown spectrum can be much faster than the time consuming look-up procedure mentioned above. Besides the increased recognition speed of the artificial neural network algorithms, these algorithms can finction with noisy spectra. Often a prerequisite for optimal artificial neural network processing, the normalization of the spectra used to train the artificial neural network is facilitated by the Raman bands associated with the internal absolute differential Raman cross section scattering standard.

A NOVEL SYSTEM FOR THE TAXONOMIC IDENTIFICATION OF BACTERIA

FIG. 1 depicts a novel system for the identification and quantification of bacteria. It is shown here that the absolute differential Raman cross-sections of bacterial Raman bands are sensitive to the H-D exchange process; although the experiments have been limited to a single pH/D condition, the patent shall not be limited to this single pH. It has been shown by other investigators, that the H-D exchange process is sensitive to pH, where solvent accessible protons exchange at a faster rate than other protons, that biomolecules such as nucleic acids and proteins exchange at different rates at a given pH/D, and that these differences in exchange rate can occur over many orders of magnitude with respect to pH/D.

It has also been shown that the addition of biomolecular denaturants, such as high salt concentrations can change the structure of proteins and nucleic acids, thus altering which chromophores that are accessible to solvent, changing their H-D exchange rate, that may in turn affect the time dependent resonance Raman spectra of the bacteria. Similarly, heating or cooling the bacteria to change the structure of the biomolecular constituents that in turn changes the population of accessible exchangeable protons, is also expected to affect the resonance Raman spectra of these species undergoing H-D exchange. Thus, this patent covers all forms of environmental perturbations of the biomolecular constituents of the bacteria to produce changes in the resonance Raman spectra of these species undergoing H-D exchange. Factors—denaturant, temperature, excitation frequencies, exchange rate—can be varied to improve quantitation and/or identification.

RESONANCE RAMAN RESPONSE SPECTRUM

FIG. 16 depicts the resonance Raman response profile. It is reasonable to expect that via manipulation of the one or more environmental parameter mentioned above, monitored as a function of time during the H-D exchange process, characteristic time dependent Raman spectra, a resonance Raman response profile, can be collected and stored in a computer that uniquely or nearly uniquely describes the species or sub-species of any bacterium. When analyzing a complicated mixture of bacteria and beef menstrua for the presence of a specific bacterial species or sub-species, the mixture can be subjected to the conditions used to produce the response profile for the species or sub-species in question, and compared to the stored response profile, to determine whether or not the bacterial species is present or not. What distinguishes this method from other spectroscopic identification and quantification methods is the manipulation of the environment to induce changes in the resonance Raman spectrum of an unknown sample, and to compare these changes to the reproducible predetermined changes in the Raman spectra of bacteria or biomolecule already studied. Thus, identification and quantification of bacteria and biomolecules isn't a static process, but rather, a dynamic one. Factors—denaturant, temperature, excitation frequencies, exchange rate—can be varied to improve quantitation and/or identification.

MULTIPLE EXCITATION FREQUENCIES AND RESONANCE RAMAN RESPONSE SPECTRA

If the Raman response profile yields ambiguous results at the excitation frequency used, another excitation frequency can be It has been shown, that resonance Raman spectra collected at different excitation frequencies exhibit preferential enhancement of protein or nucleic acid constituents, at 222 nm excitation, bacterial protein vibrational bands are enhanced, while at 240 nm excitation, bacterial nucleic acid are enhanced. The combination of excitation frequency and the time dependent effects of the H-D exchange process (with or without environmental perturbation) on the resonance Raman spectrum, will likely allow for a unique resonance Raman taxonomic description of any bacterium to be obtained.

GENERAL BIOMOLECULAR IDENTIFICATION—VIRUSES, TISSUES, ETC

Although this invention is aimed at addressing the identification of meat and poultry bacterial pathogens, it should not be limited to bacterial pathogens found on these substrates. This invention should be useful in the identification and quantification of any biomolecular assembly found on any substrate, including viruses and fungi. The substrate could include and biomolecular tissue or any substrate including walls, tabletops, cooking utensils, etc.

USE IN NONBIOLOGICAL SYSTEMS THAT HAVE EXCHANGEABLE PROTONS

The time dependence of the exchange of proton for deuterons manifested in the resonance Raman spectrum or spectra of the species in question, coupled with the excitation frequency dependence of the resonance Raman spectrum may used to quantify and identify any species with exchangeable protons, such as plastics and inorganic materials.

It will be appreciate by those of ordinary skill in the art that various changes and modifications may be made to the description and drawings without departing from the spirit and scope of the present invention. For example, whereas the Raman collection geometry discussed above is a backscattering, other geometries could be employed to acquire the Raman spectra 22.

I claim:

1. A method of resonance Raman spectroscopy for identifying and quanitating proton-bearing analytes including bacteria, viruses, prions, biomolecules, biomolecular assemblies, inorganic and organic compounds comprising:

deuterating with dideuterium oxide (D20) a sample containing one or more analytes, each analyte having exchangeable protons such that said deuteration will cause the protons of said analyte to be exchanged with deuterons;

providing a monochromatic light at an excitation frequency onto a sample for producing Raman sample light and rejecting Rayleigh light;

passing said Raman sample light through a depolarizer for producing randomized polarization components of said Raman sample light;

generating a Raman sample spectrum calibrated with respect to an absolute differential Raman cross-section standard in response to said randomized polarization components;

providing said Raman sample spectrum to a spectral analyzer;

provides the identity of analytes in the sample.

2. The method of claim 1, wherein the step of providing the identity of the analytes in the sample includes performing an instrument efficiency correction in response to the Raman sample spectrum.

3. The method of claim 1, wherein the step of providing the identity of the analytes in the sample includes performing a self absorption correction in response to the Raman sample spectrum.

4. The method of claim 1, wherein the step of providing the identity of the analytes in the sample includes performing a solid angle correction in response to the Raman sample spectrum.

5. The method of claim 1, wherein the step of providing the identity of the analytes in the sample includes performing a local-field correction in response to the Raman sample spectrum.

6. The method of claim 1, further comprising passing said Raman light through a polarizer for getting a perpendicular component spectrum and a parallel component spectrum for providing a depolarization ratio of of a Raman analyte band for the identification of said analytes.

7. The method of claim 1, further comprising passing said Raman light through a polarizer for getting a perpendicular component spectrum and a parallel component spectrum for providing a depolarization ratio of of a Raman analyte band for the identification of said analytes and wherein said perpendicular components are provided in response to a calculated, corrected perpendicular component for providing a depolarization ratio of of a Raman analyte band for the identification of said analytes.

8. The method of claim 1 wherein the extent of said deuteration is varied for increasing the speed of said identification including manipulating the extent of deuteration of said analytes;
causing thereby Raman bands of a plurality of said analytes to become different;
identifying said analytes on the basis of said difference.

9. The method of claim 1, wherein Raman sample spectra are taken at multiple exhange rates for providing said Raman sample spectra at said multiple exchange rates to said spectral analyzer.

10. The method of claim 1, wherein the excitation frequency is constant for providing said Raman sample spectra at said constant excitation frequency to said spectral analyzer.

11. The method of claim 1, wherein spectra of the sample are taken at multiple excitation frequencies for providing said Raman sample spectra at said multiple excitation frequencies to a spectral analyzer.

12. The method of claim 1, wherein the sample is deuterated at a fixed temperature for providing said Raman sample spectra at said multiple exchange rates to a spectral analyzer.

13. The method of claim 1, wherein the sample is deuterated at mutiple temperatures for providing said Raman sample spectra at said multiple exchange rates to a spectral analyzer.

14. The method of claim 1, wherein said identification occurs as a function of denaturant.

15. The method of claims 1, wherein said sample is retained in a sampling apparatus, comprising:

a reservoir for of said sample;
a pump for continuously drawing said analyte;
a planar flow device having a windowless sample stream between a pair of bookends said pair having a first end and a second end such that said analyte is continously flowing from said pump into the first end, between said bookends for being exposed to said monochromatic light, wherein the angle of the normal of said windowless sample stream is beteween 0 and 90 degrees with respect to the collection optic for rejecting Rayleigh scattering, and exiting said planar flow device.

16. A method of resonance Raman spectroscopy for identifying and quanitating proton-bearing analytes including bacteria, viruses, prions, biomolecules, biomolecular assemblies, inorganic and organic compounds comprising:

deuterating with dideuterium oxide (D20) a sample containing one or more analytes, each analyte having exchangeable protons such that said deuteration will cause the protons of said analyte to be exchanged with deuterons;
providing a monochromatic light at an excitation frequency onto a sample for producing Raman sample light and rejecting Rayleigh light;
passing said Raman sample light through a depolarizer for producing randomized polarization components of said Raman sample light;
generating a Raman sample spectrum calibrated with respect to an absolute differential Raman cross-section standard in response to said randomized polarization components;
providing said Raman sample spectrum to a spectral analyzer;

providing the quantity of analyte in said sample.

17. The method of claim 16, wherein the step of providing the identity of the analytes in the sample includes performing an instrument efficiency correction in response to the Raman sample spectrum.

18. The method of claim 16, wherein the step of providing the identity of the analytes in the sample includes performing a self absorption correction in response to the Raman sample spectrum.

19. The method of claim 16, wherein the step of providing the identity of the analytes in the sample includes performing a solid angle correction in response to the Raman sample spectrum.

20. The method of claim 16, wherein the step of providing the identity of the analytes in the sample includes performing a local-field correction in response to the Raman sample spectrum.

21. The method of claim 16, further comprising passing said Raman light through a polarizer for getting a perpendicular component spectrum and a parallel component spectrum for providing a depolarization ratio of of a Raman analyte band for the identification of said analytes.

22. The method of claim 16, further comprising passing said Raman light through a polarizer for getting a perpendicular component spectrum and a parallel component spectrum for providing a depolarization ratio of of a Raman analyte band for the identification of said analytes and wherein said perpendicular components are provided in response to a calculated, corrected perpendicular component for providing a depolarization ratio of of a Raman analyte band for the identification of said analytes.

23. The method of claim 16 wherein the extent of said deuteration is varied for increasing the speed of said identification including manipulating the extent of deuteration of said analytes;
causing thereby Raman bands of a plurality of said analytes to become different;
identifying said analytes on the basis of said difference.

24. The method of claim 16, wherein Raman sample spectra are taken at multiple exhange rates for providing said Raman sample spectra at said multiple exchange rates to said spectral analyzer.

25. The method of claim 16, wherein the excitation frequency is constant for providing said Raman sample spectra at said constant excitation frequency to said spectral analyzer.

26. The method of claim 16, wherein spectra of the sample are taken at multiple excitation frequencies for providing said Raman sample spectra at said multiple excitation frequencies to a spectral analyzer.

27. The method of claim 16, wherein the sample is deuterated at a fixed temperature for providing said Raman sample spectra at said multiple exchange rates to a spectral analyzer.

28. The method of claim 16, wherein the sample is deuterated at mutiple temperatures for providing said Raman sample spectra at said multiple exchange rates to a spectral analyzer.

29. The method of claim 16, wherein said identification occurs as a function of denaturant.

30. The method of claims 16, wherein said sample is retained in a sampling apparatus, comprising:

a reservoir for of said sample;

a pump for continuously drawing said analyte;

a planar flow device having a windowless sample stream between a pair of bookends said pair having a first end and a second end such that said analyte is continously flowing from said pump into the first end, between said bookends for being exposed to said monochromatic light, wherein the angle of the normal of said windowless sample stream is between 0 and 90 degrees with respect to the collection optic for rejecting Rayleigh scattering, and exiting said planar flow device.

* * * * *